United States Patent
Cai et al.

(10) Patent No.: US 8,426,028 B2
(45) Date of Patent: Apr. 23, 2013

(54) PREPARATION OF SENSORS ON OLIGO- OR POLY (ETHYLENE GLYCOL) FILMS ON SILICON SURFACES

(75) Inventors: Chengzhi Cai, Houston, TX (US); Chin Ming Yam, Stafford, TX (US); Jianhua Gu, Houston, TX (US)

(73) Assignee: University of Houston, Houston, TX (US)

( * ) Notice: Subject to any disclaimer, the term of this patent is extended or adjusted under 35 U.S.C. 154(b) by 536 days.

(21) Appl. No.: 12/108,217

(22) Filed: Apr. 23, 2008

(65) Prior Publication Data

US 2009/0082222 A1    Mar. 26, 2009

Related U.S. Application Data

(63) Continuation-in-part of application No. 11/587,232, filed as application No. PCT/US2005/014391 on Apr. 27, 2005.

(60) Provisional application No. 60/566,120, filed on Apr. 28, 2004, provisional application No. 60/913,431, filed on Apr. 23, 2007.

(51) Int. Cl.
  *B32B 27/32*   (2006.01)
  *B32B 9/04*   (2006.01)
  *B32B 13/04*   (2006.01)
  *C07H 19/00*   (2006.01)
  *C07H 21/00*   (2006.01)
  *C07H 21/02*   (2006.01)
  *A61K 48/00*   (2006.01)

(52) U.S. Cl.
  USPC .......... 428/446; 428/220; 428/448; 502/158; 514/44 R; 536/22.1; 536/23.1

(58) Field of Classification Search .............. 428/220, 428/446, 448; 502/158; 514/44 R; 536/22.1; 536/23.1
See application file for complete search history.

(56) References Cited

U.S. PATENT DOCUMENTS 5,973,124 A   10/1999 Bayer et al.
6,183,990 B1   2/2001 Duecker et al.
(Continued)

FOREIGN PATENT DOCUMENTS
WO PCT/US2005/014391   * 12/2005

OTHER PUBLICATIONS

Zhang et al., "Carbohydrate-Protein Interactions by "clicked" Carbohydrate Self Assembled monolayers", Analytical Chemistry, vol. 78, No. 6, (Mar. 2006), pp. 2001-2008.*

(Continued)

*Primary Examiner* — Jonathan Langman
(74) *Attorney, Agent, or Firm* — Winstead PC

(57) ABSTRACT

A sensor that includes a) a silicon (Si) substrate having a surface; and b) a monolayer of oligoethylene glycol (OEG) bonded to the surface via silicon-carbon bonds. Regions of the OEG monolayer distal to the surface are functionalized with a ligand serving as a recognition element for a bioanalyte. The ligand is covalently bonded in these regions as a cycloadduct of a 1,3-dipolar cycloaddition reaction. A method of making a silicon surface that recognizes a biological specimen includes 1) hydrosilylating with a mixture that includes an oligoethylene glycol (OEG) substituted with an alkene at one end of the OEG and capped at the opposing end of the OEG and an oligoethylene glycol (OEG) substituted with an alkene at one end of the OEG and an alkyne having a protecting group at the opposing end of the OEG and 2) removing the protecting group from the alkyne; and 3) reacting the alkyne with a reagent in a 1,3-dipolar cycloaddition. The reagent in the 1,3-dipolar cycloaddition includes a portion capable of being recognized by a biological specimen.

16 Claims, 25 Drawing Sheets

U.S. PATENT DOCUMENTS

2004/0152826 A1 8/2004 Therien et al.
2004/0253184 A1 12/2004 Li et al.

OTHER PUBLICATIONS

Sun et al., "Carbohydrate and Protein Immobilization onto Solid Surfaces by Sequential Diels-Alder and Azide-Alkyne Cycloadditions", Bioconjugate Chem., (2006), vol. 17, pp. 52-57.*

Kim et al., "Electrochemical Deprotection for Site Selective Immobilization of Biomolecules", Langmuir, (2002), vol. 18, pp. 1460-1462.*

Svedhem et al., Synthesis of a series of oligo(ethylene glycol)-terminated alkanethiol amides designed to address structure and stability of biosensing interfaces. Journal of Organic Chemistry, 2001, vol. 66, pp. 4494-4503.

Yam et al., Modification of silicon AFM cantilever tips with an oligo(ethylene glycol) derivative for resisting proteins and maintaining a small tip size for high-resolution imaging. Journal of the American Chemical Society, 2003, vol. 125, pp. 7498-7499.

Stewart et al., Photopatterned hydrosilylaation on porous silicon. Angew. Chem. Int. Ed. 1998, vol. 37, No. 23, pp. 3257-3260.

Maoz et al., "Constructive Nanolithography": Insert monolayers as patternable templates for in-situ nanofabrication of metal-semiconductor-organic surface structures—A generic approach. Adv. Mater. 2000, vol. 12, No. 10, pp. 725-731.

Seidel et al. Miniaturization and parallelization of fluorescence immunoassays in nanoliter plates. Trends in Analytical Chemistry, 2003, vol. 22, No. 6, pp. 385-394.

Gu, Jianhua, et al., "Nanometric protein arrays on protein-resistant monolayers on silicon surfaces," Journal of the American Chemical Society, Jul. 7, 2004, vol. 126, No. 26, pp. 8098-8099.

Ciampi, Simone, et al., "Functionalization of acetylene-terminated monolayers on Si(100) surfaces: a click chemistry approach," Langmuir: The ACS Journal of Surfaces and Colloids, Aug. 28, 2007, vol. 23, No. 18, pp. 9320-9329.

Rohde, et al., "Non-Oxidative Approach toward Chemically and Electrochemically Functionalizing Si(111)," J. Am. Chem. Soc., vol. 128, Jan. 1, 2006, pp. 9518-9525.

Meldal, Morten, et al., "Cu-catalyzed azide-alkyne cycloaddition," Chemical Reviews, Aug. 2008, vol. 108, No. 8, pp. 2952-3015.

International Preliminary Report on Patentability, PCT/US2005/014391, dated Nov. 9, 2006.

Linford, et al., "Alkyl Monolayers on Silicon Prepared from 1-Alkenes and Hydrogen-Terminated Silicon," 117 Am. Chem. Soc. 3145 (1995).

Cicero, et al., "Photoreactivity of Unsaturated Compounds with Hydrogen-Terminated Silicon (111)," 16 Langmuir 5688 (2000).

Cavalli, Silvia, et al., "The chemical modification of liposome surfaces via a copper-mediated [3+2] azide-alkyne cycloaddition monitored by a colorimetric assay," Chem. Commun., Supplementary Material, 2006.

Lallana, Enrique, et al., "Click Chemistry for Drug Delivery Nanosystems," Pharm Res (2012) 29:1-34.

Gal, Sigal et al., "Peroxidation of liposomal palmitoyl-linoleoylphosphatidylcholine (PLPC), effects of surface charge on the oxidizability and on the potency of antioxidants," Chemistry and Physics of Lipids 126 (2003) 95-110.

Copper(I) bromide, http://en.wikipedia.org/wiki/Copper(I)_bromide (Jun. 4, 2012).

Gupta, Sayam Sen, et al., "Virus-glycopolymer conjugates by copper(I) catalysis of atom transfer radical polymerization and azide-alkyne cycloaddition," Chem. Commun., 2005, pp. 4315-4317.

Cavalli, Silvia, et al., "The chemical modification of liposome surfaces via a copper-mediated [3+2] azide-alkyne cycloaddition monitored by a colorimetric assay," Chem. Commun., 2006, pp. 3193-3195.

Binder, et al., "'Click' Chemistry in Polymer and Materials Science," Macromol. Rapid Commun. 2007, 28, pp. 15-54.

Hassane, Fatouma Said, et al., "Targeted Liposomes: Convenient Coupling of Ligands to Preformed Vesicles Using Click Chemistry," Bioconjugate Chem. 2006, vol. 17, No. 3, pp. 849-854.

Lewis, Warren G. et al., "Discovery and Characterization of Catalysts for Azide-Alkyne Cycloaddition by Fluorescence Quenching," J. Am. Chem. Soc. 2004, vol. 126, No. 30, pp. 9152-9153.

Lutz, Jean-Francois, "1,3-Dipolar Cycloadditions of Azides and Alkynes: A Universal Ligation Tool in Polymer and Materials Science," Angew. Chem. Int. Ed. 2007, 46, pp. 1018-1025.

Opsteen, Joost A., et al., "'Clickable' polymersomes," Chem. Commun., Aug. 14, 2007, No. 30, pp. 3136-3138.

Rodionov, Valentin O., et al., "Benzimidazole and Related Ligands for Cu-Catalyzed Azide-Alkyne Cycloaddition," J. Am. Chem. Soc., vol. 129, No. 42, 2007, pp. 12696-12704.

Wang, Qian, et al., "Bioconjugation by Copper(I)-Catalyzed Azide-Alkyne [3+2] Cycloaddition," J. Am. Chem. Soc., vol. 125, No. 11, 2003, pp. 3192-3193.

TR Chan, "Triazoles in Click Chemistry: Ligands, Copper (I)-Catalysis, and Organocatalysis." PhD Thesis, The Scripps Research Institute. May 2005, pp. two title pages, pp. i-xvi and 1-176.

Chan, T.R. et al., "Polytriazoles as Copper(I)-Stabilizing Ligands in Catalysis," Organic Letters, 2004, vol. 6, No. 17, 2853-2855.

* cited by examiner

US 8,426,028 B2

PREPARATION OF SENSORS ON OLIGO- OR POLY (ETHYLENE GLYCOL) FILMS ON SILICON SURFACES

CROSS-REFERENCE TO RELATED APPLICATIONS

This application is a continuation-in-part of U.S. patent application Ser. No. 11/587,232 filed Oct. 23, 2006 which is the national stage entry of PCT No. PCT/US05/14391 filed Apr. 27, 2005, which in turn claims priority to U.S. Provisional Application No. 60/566,120 filed Apr. 18, 2004. This Application also claims priority to U.S. Provisional Application No. 60/913,431, filed Apr. 23, 2007. All the aforementioned applications are incorporated by reference herein in their entirety.

STATEMENT OF FEDERALLY SPONSORED RESEARCH

This invention was made, in part, with support from the National Science Foundation, Grant Number CTS-0210840; and the Robert A. Welch Foundation, Grant Number 1-5-57897.

BACKGROUND

Microarray technology has been widely used for genomics and proteomics research as well as for drug screening. Currently, the spot size in most microarrays is larger than one micron. The use of nanometric biomolecular arrays, with smaller spot sizes, will enable high-throughput screening of biomolecules—eventually at the single molecule level. Also, nanometric arrays permitting precise control over the position and orientation of individual molecules will become a powerful tool for studying multi-valent and/or multi-component molecular interactions in biological systems. Toward these ends, protein arrays with feature sizes smaller than 100 nm have been fabricated, mostly using dip-pen nanolithography and nanografting. [See Lee et al., Science 2002, vol. 295, p. 1702; Wilson et al., Proc. Natl. Acad. Sci. USA 2001, vol. 98, p. 13660; Liu et al., Proc. Natl. Acad. Sci. USA 2002, vol. 99, p. 5165; Pavlovic et al., Nano Lett. 2003, vol. 3, p. 779; and Krämer et al., Chem. Rev. 2003, vol. 103, p. 4367.]

Modification of silicon surfaces with organic thin films to allow strong and highly specific interactions with targeted biological entities is of tremendous interest in the fields of biomicroelectrical mechanical systems (bioMEMS) that may integrate biosensing with controlled delivery of drugs. Target molecules interacting with the film surfaces can be detected optically, mechanically, magnetically, electronically or the combination. [Grayson, A. C. R.; Shawgo, R. S.; Johnson, A. M.; Flynn, N. T.; Li, Y. W.; Cima, M. J.; Langer, R. "A BioMEMS review: MEMS technology for physiologically integrated devices." Proc. IEEE 2004, 92, 6-21.]

BioMEMS are of tremendous interest for their potential applications in microscale, high throughput biosensing and medical devices [Shawgo et al., J. Curr. Opin. Solid State Mater. Sci. 2002, v. 6, p. 329]. Using silicon as a substrate for the preparation of such devices is particularly attractive, since the extensive micro-fabrication techniques developed by the microelectronic industries can be used to fabricate and integrate various micro-components into the devices. For reducing biofouling, considerable research has been directed to the modification of substrate surfaces with stable and ultrathin films of poly(ethylene glycol) (PEG) or oligo(ethylene glycol) (OEG) [Prime et al., Science 1991, vol. 252, p. 1164].

Since many of the ultimate applications for bio-devices require moderate-term (e.g., a few hours to several days) exposure to biological media (e.g., buffer of pH 7.4 at 37° C.), stability of the bio-compatible coatings on the devices under these conditions is highly desirable. All of the OEG/PEG-terminated films on silicon substrates reported by others are bound onto the silicon surfaces via Si—O bonds that are prone to hydrolysis [Calistri-Yeh et al., Langmuir 1996, v. 12, p. 2747), thereby limiting their stability under physiological conditions (Sharma et al., Langmuir 2004, v. 20, p. 348].

For implantable bioMEMS, inflammatory responses often lead to device failure due to the formation of a thick layer of fibrous cells on the implant. [Wilson, G. S.; Gifford, R. "Biosensors for real-time in vivo measurements." Biosens. Bioelectron. 2005, 20, 2388-2403.] The initial step of inflammatory response is the non-specific adsorption of proteins onto the substrates. This step alone may greatly lower the sensitivity and specificity of the implanted sensor. Therefore, ideal coating for silicon based biosensors should be 1) ultrathin for high sensitivity; 2) resistant to non-specific interactions with proteins and cells in body fluids and tissues; 3) strongly and specifically interacting with target molecules or cells; 4) stable over a period of time required by specific applications under in vivo conditions.

In addition to bioMEMS applications, ultraflat, stable and highly protein-resistant films on silicon surfaces represent ideal platforms for fabrication of single molecule arrays presenting signaling and adhesion molecules. These well-defined model systems allow for fundamental study of cell response to chemical signals at a single molecule level. A deeper understanding of how the nanoscale presentation of such molecules determine cellular functions, such as differentiation, proliferation and apoptosis, [Arnold, M.; Cavalcanti-Adam, E. A.; Glass, R.; Blummel, J.; Eck, W.; Kantlehner, M.; Kessler, H.; Spatz, J. P. "Activation of integrin function by nanopatterned adhesive interfaces." Chem Phys Chem 2004, 5, 383-388; Maheshwari, G.; Brown, G.; Lauffenburger, D. A.; Wells, A.; Griffith, L. G. "Cell adhesion and motility depend on nanoscale RGD clustering." J. Cell Sci. 2000, 113, 1677-1686.] is of tremendous importance for designing the next generation biomaterials, implantable bioMEMEs and pharmaceuticals.

SUMMARY

The present disclosure is generally directed to sensors, and to methods of making such sensors.

In some aspects, embodiments disclosed herein relate to a sensor that includes a) a silicon (Si) substrate having a surface; and b) a monolayer of oligoethylene glycol (OEG) bonded to the surface via silicon-carbon bonds. Regions of the OEG monolayer distal to the surface are functionalized with a ligand serving as a recognition element for a bioanalyte. The ligand is covalently bonded in these regions as a cycloadduct of a 1,3-dipolar cycloaddition reaction.

A method of making sensors, in accordance with embodiments disclosed herein, involves 1,3 dipolar cycloaddition reactions between a ligand possessing a functional group (or precursor) 1,3 dipolar species and a carbon-carbon unsaturation displayed at the distal end of an oligoethylene glycol attached at the proximal end to a silicon surface. The present disclosure is also directed to methods of using such sensors in arrays, especially in biosensors.

In other aspects, embodiments disclosed herein relate to a method of making a silicon surface that recognizes a biological specimen. The method includes 1) hydrosilylating with a mixture that includes an oligoethylene glycol (OEG) substituted with an alkene at one end of the OEG and capped at the opposing end of the OEG and an oligoethylene glycol (OEG) substituted with an alkene at one end of the OEG and an alkyne having a protecting group at the opposing end of the OEG and 2) removing the protecting group from the alkyne; and reacting the alkyne with a reagent in a 1,3-dipolar cycloaddition. The reagent in the 1,3-dipolar cycloaddition includes a portion capable of being recognized by a biological specimen.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
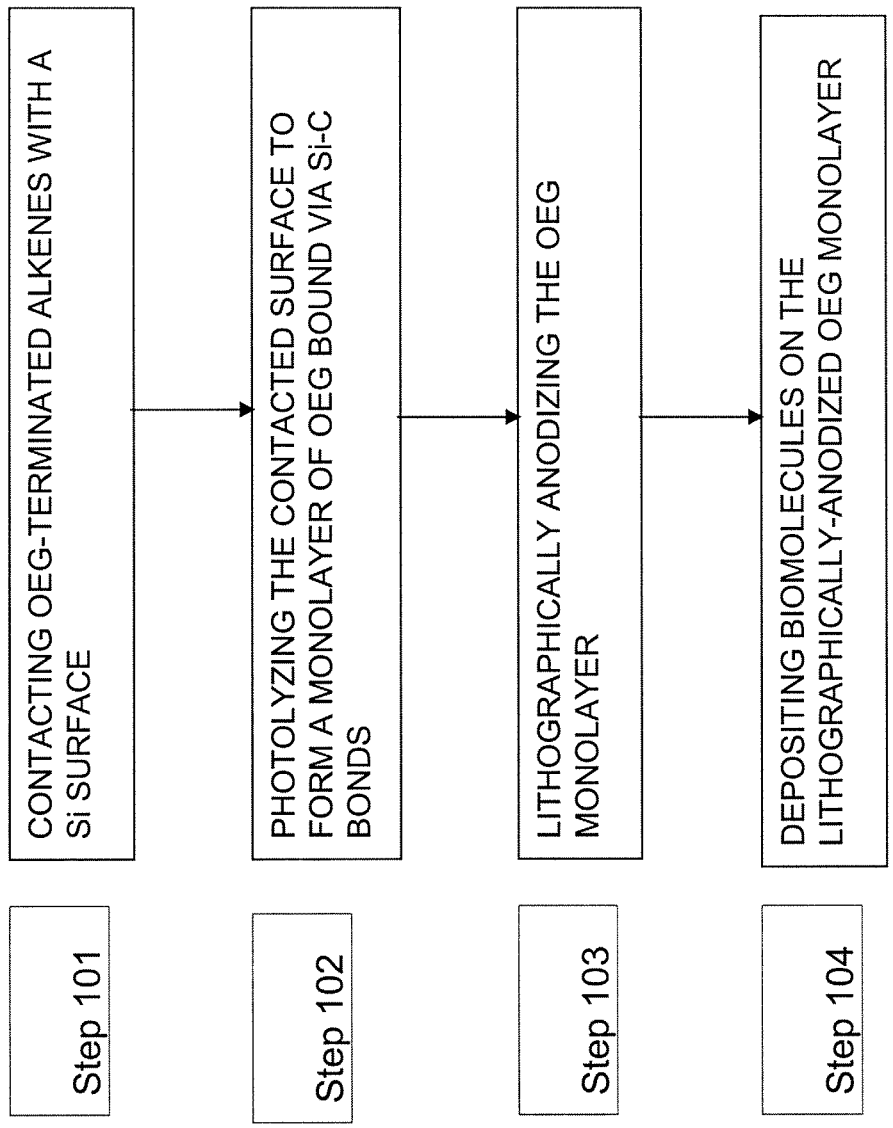
FIG. 1 depicts, schematically, a method of making nanometric biomolecular arrays, in accordance with embodiments disclosed herein.

In accordance with embodiments of the present disclosure, a sensor includes a) a silicon (Si) substrate having a surface; and b) a monolayer of oligoethylene glycol (OEG) bonded to the surface via silicon-carbon bonds. Regions of the monolayer distal to the surface are functionalized with a ligand serving as a recognition element for a bioanalyte. This ligand is generally covalently bonded to the OEG terminal end distal to the silicon surface as a cycloadduct of a 1,3-dipolar cycloaddition reaction.

In some embodiments, the ligand is a biomolecule such as carbohydrates, proteins, oligonucleotides, and combinations thereof. In a particular embodiment the biomolecule is mannose. Utilizing mannose as the ligand, the sensor is capable of recognizing *E. Coli* as the bioanalyte.

In some embodiments, a method of modifying a silicon surface includes hydrosilylating with a mixture of an oligoethylene glycol (OEG) substituted with an alkene at one end of the OEG and protected at the opposing end of the OEG and an OEG substituted with an alkene at one end of the OEG and an alkyne having a protecting group at the opposing end of the OEG. This hydrosilylation bonds the OEG to the silicon surface via a carbon silicon bond. After removing the protecting group from the alkyne a 1,3-dipolar cycloaddition is performed.

The 1,3-dipolar cycloaddition may utilize an azide, a nitrile oxide, an azomethine ylide, a carbonyl ylide, or a nitrone. In particular embodiments, the 1,3-dipolar cycloaddition is executed with an azide. 1,3-dipolar species that can participate in these reactions are characterized as three atom zwitterionic compounds having a resonance stabilized form that distributes a formal positive charge at one end (atom 1 or 3) of the three atom array and a formal negative charge at the opposite end (atom 3 or 1) of the three atom array.

In still further embodiments, the present disclosure provides a method of bioconjugation to a silicon surface that includes 1) hydrosilylating with a mixture that includes an oligoethylene glycol (OEG) substituted with an alkene at one end of the OEG and protected at the opposing end of the OEG and an oligoethylene glycol (OEG) substituted with an alkene at one end of the OEG and an alkyne having a protecting group at the opposing end of the OEG 2) removing the protecting group from the alkyne; and 3) reacting the alkyne with a reagent in a 1,3-dipolar cycloaddition. The reagent in the 1,3-dipolar cycloaddition may include a modified biomolecule. The modified biomolecule may include a reactive functional group such as an azide, a nitrile oxide, an azomethine ylide, a carbonyl ylide, or a nitrone. In particular embodiments the modified biomolecule has an azide as the reactive functional group.

The methods described herein may be useful in making a silicon surface that recognizes a biological specimen. To do so the method may include 1) hydrosilylating with a mixture comprising: an oligoethylene glycol (OEG) substituted with an alkene at one end of the OEG and capped at the opposing end of the OEG; and an oligoethylene glycol (OEG) substituted with an alkene at one end of the OEG and an alkyne having a protecting group at the opposing end of the OEG; 2) removing the protecting group from the alkyne; and 3) reacting the alkyne with a reagent in a 1,3-dipolar cycloaddition. The reagent in the 1,3-dipolar cycloaddition includes a portion capable of being recognized by a biological specimen.

The 1,3-dipolar cycloaddition further includes the use of a reactive functional group, for example, an azide, a nitrile oxide, an azomethine ylide, a carbonyl ylide, or a nitrone. In particular embodiments, the reactive functional group is an azide. The biological specimen may be a bacterium, a virus, a protein, a DNA sequence, a RNA sequence, or an oligosaccharide.

A silicon surface modified to interact with a biological specimen made by the process comprising: hydrosilylating with a mixture comprising: an oligoethylene glycol (OEG) substituted with an alkene at one end of the OEG and capped at the opposing end of the OEG; and an oligoethylene glycol (OEG) substituted with an alkene at one end of the OEG and an alkyne having a protecting group at the opposing end of the OEG; removing the protecting group from the alkyne; and reacting the alkyne with a reagent in a 1,3-dipolar cycloaddition; wherein the reagent in the 1,3-dipolar cycloaddition comprises a portion capable of being recognized by a biological specimen.

In some embodiments, methods of generated an array of biomolecules on a Si surface includes: (a) contacting OEG-terminated alkenes with a hydrogen-terminated Si surface to form a contacted surface; (b) photolyzing the contacted surface to effect Si—C bonding between the OEG-terminated alkenes and the Si surface and form an OEG-coated Si surface comprising a monolayer of OEG bound to the Si surface through Si—C bonds; (c) anodizing regions on the top of the OEG monolayer of the OEG-coated Si surface via AFM anodization lithography to yield a nanolithographically-patterned OEG-coated Si surface comprising regions with enhanced associability toward biomolecules; and (d) depositing at least one type of biomolecule in the regions of enhanced associability to form a nanometric biomolecular array.

Generally, the nanometric biomolecular arrays made by the above-described methods comprise: (a) a Si substrate; (b) a monolayer of OEG bonded to the Si substrate via Si—C bonds, wherein regions at the top of the monolayer have been lithographically-patterned; and (c) biomolecules associated with the lithographically-patterned regions of the OEG monolayer.

In some embodiments, the present invention provides a novel approach for preparation of nanometric protein arrays, based on binding of biomolecules to nano-templates generated by AFM anodization lithography on robust, ultrathin monolayers terminated with oligo(ethylene glycol) (OEG) derivatives with the general formula of —$(CH_2CH_2O)_n$—R ($n>1$, R=$CH_3$, H, etc.) on conducting silicon surfaces. A specific example is the preparation of nanometric avidin arrays. Applicants have shown that biotinated-BSA, but not the native BSA, binds to the avidin arrays, and the resulting arrays of biotinated-BSA can bind avidin to form protein dots with a feature sizes of ~30 nm, scalable down to the size of a single protein molecule.

Such nanometric arrays have at least the following unique advantages: (a) they will vastly improve the detection sensitivity (down to a single molecule), allowing for detection of biomolecular variations correlated with diseases, which are typically expressed at very low level; (b) they will tremendously increase the probe density on a chip (e.g., incorporating the whole human genome in the same chip); (c) they permit a label-free detection of the binding of target molecules on the nanoarrays; (d) they greatly shorten the time for binding of target molecules to the nanoarrays and improve the efficiency of the binding; (e) they may substantially improve the specificity of the detection; (f) the single molecule arrays will greatly facilitate single molecule sequencing of DNA using polymerase and nucleotides that are fluorescently labeled, and single molecule arrays of the template and the polymerase will reduce the background fluorescence and greatly improve the quality of the data; and such (g) nanometric arrays will become a powerful research tool for studying the cooperative interaction among multiple biomolecules. It should be noted that advantages (a)-(e) can be gained only for nanoarrays where the spot size is less than about 25 nm and comprising only one or a handful of probe molecules.

In some embodiments, the present disclosure is generally directed to nanometric biomolecular arrays and to a novel approaches for preparation of such nanoarrays, based on binding of biomolecules, such as avidin, to templates generated by AFM anodization lithography (conductive AFM) on biocompatible ultrathin films on silicon substrates. In some embodiments, such films are generally robust, ultrathin monolayers terminated with oligo(ethylene glycol) (OEG) with the general formula of —$(CH_2CH_2O)_n$—R ($n>1$, R=$CH_3$, H, etc.) on conducting silicon surfaces, wherein such films have been nanolithographically-patterned using conductive AFM lithography (Maoz et al., *Adv. Mater.* 2000, vol. 12, p. 725). The lithography process is followed by chemical and biochemical derivatization of the resulting nanopatterns. The unique features of this approach include: (a) the OEG-monolayers resist non-specific adsorption and denaturing of proteins on the templates; (b) conductive AFM can be used to selectively oxidize the top portion of the OEG-monolayer to generate carboxylic acids, aldehydes, alcohols and other functional groups that can be used to attach biomolecules; (c) the monolayers are attached to silicon substrates via Si—C bonds with a high density, rendering the system highly robust; and (d) the lithography process is very rapid. In a specific example, the resulting avidin arrays have a feature size of ~26 nm, and they can serve as templates for the preparation of nanoarrays of a wide variety of proteins that are site-specifically labeled with biotin [Lue et al., J. Am. Chem. Soc. 2004, v. 126, p. 1055].

As described in commonly assigned, co-pending U.S. patent application Ser. No. 10/742,047, olig(ethylene glycol) (OEG) terminated alkenes were grafted onto hydrogen-terminated silicon surfaces through hydrosilylation (as developed by Linford and Chidsey, see Linford et al., J. Am. Chem. Soc. 1993, v. 115, p. 12631; Buriak, Chem. Rev. 2002, v. 102, p. 1271) forming robust Si—C bonds with the silicon surfaces. It was shown that the alkyl monolayers grown by this method were stable in boiling organic solvents, water, and acids, as well as slightly basic solutions [Linford et al., J. Am. Chem. Soc. 1995, v. 117, p. 3145]. A method describing the modification of hydrogen-terminated silicon surfaces, including a silicon atomic force microscopy (AFM) cantilever tip, with OEG-terminated alkenes via either thermally- or photo-induced hydrosilylation is also found in commonly assigned, co-pending U.S. patent application Ser. No. 10/742,047. [See also Yam et al., J. Am. Chem. Soc. 2003, v. 125, p. 7498; Yam et al., Chem. Commun., 2004, p. 2510]. The efficiency with which such OEG-terminated films resist protein adsorption depends on many factors including the number of ethylene glycol (EG) units and the packing density of the films that is determined by the underlying substrate surface and the deposition methods. For example, OEG-terminated thiolate self-assembled monolayers (SAMs) on gold (111) surfaces are protein resistant, but those on silver (111) surfaces are not [Herrwerth et al., J. Am. Chem. Soc. 2003, vol. 125, p. 9359]. The latter was attributed to the high packing density and structural ordering of the SAMs. Research has demonstrated that films grown on Si(111) surfaces had a density similar to that of the corresponding thiolate SAMs on gold (111) surfaces, and similarly reduced the adsorption of fibrinogen to 1% monolayer or less.

Referring to FIG. 1, in some embodiments, such above-mentioned methods generally comprise the steps of: (Step 101) contacting OEG-terminated alkenes with a hydrogen-terminated Si surface to form a contacted surface; (Step 102) photolyzing the contacted surface to effect Si—C bonding between the OEG-terminated alkenes and the Si surface and form a OEG-coated Si surface comprising a monolayer of OEG bound to the Si surface through Si—C bonds; (Step 103) lithographically anodizing regions on the top of the OEG monolayer of the OEG-coated Si surface via AFM anodization lithography to yield a nanolithographically-patterned OEG-coated Si surface comprising regions with enhanced associability toward biomolecules; and (Step 104) depositing at least one type of biomolecule in the regions of enhanced associability to form a nanometric biomolecular array.

In some embodiments, the OEG-terminated alkenes comprise EG sequences selected from the group consisting of $EG_1$-$EG_{20}$, and combinations thereof, wherein "n" in $EG_n$ describes the number of —($CH_2CH_2O$)— repeat units. In some or other embodiments, the OEG-terminated alkenes comprise PEG-terminated alkenes, wherein PEG-terminated alkenes comprise $EG_n$ sequences of $n>20$.

Typically, the Si surface is atomically flat. In some embodiments the Si surface is selected from the group consisting of (100), (111), and combinations thereof. In some embodiments, upon coating the Si surface with an OEG monolayer, the OEG-coated Si surface is washed, and optionally dried, prior to lithographically anodizing regions on top of it.

In some embodiments, the nanolithographically-patterned (anodized) regions of the OEG-coated Si surface comprise nanowells (i.e., "spots"). In some embodiments, the nanolithographically-patterned regions of the OEG-coated Si surface comprise carboxylic acid, aldehyde, alcohol, and/or other moieties, wherein these moieties provide, at least in part, the enhanced associability toward biomolecules.

In some embodiments, the at least one type of biomolecule is selected from the group consisting of proteins, oligonucleotides, and combinations thereof. Avidin is an exemplary such biomolecule. In some embodiments, at least some of the at least one type of biomolecule binds with the regions of enhanced associability via amide bonds.

Generally, the nanometric biomolecular arrays made by the above-described methods comprise: (a) a Si substrate; (b) a monolayer of OEG bonded to the Si substrate via Si—C bonds, wherein regions at the top of the monolayer have been lithographically-patterned; and (c) biomolecules associated with the lithographically-patterned regions of the OEG monolayer.

Typically, the above-mentioned Si surface is atomically flat. In some embodiments, the Si surface is selected from the group consisting of (100), (111), and combinations thereof. In some embodiments, the OEG bound to the Si surface comprises EG sequences selected from the group consisting of $EG_1$-$EG_{20}$, and combinations thereof. As mentioned above, such OEG is bound to the surface through Si—C bonds.

In some embodiments, the biomolecules (as part of the array) are selected from the group consisting of proteins, oligonucleotides, and combinations thereof. Avidin is an exemplary such molecule. Typically, the biomolecules are associated by a bonding means selected from the group consisting of covalent bonding, ionic bonding, electrostatic forces, and combinations thereof. In some particular embodiments, the biomolecules are associated with the lithographically-patterned regions of the OEG monolayer via amide bonds.

In some embodiments, the nanometric biomolecular array is operable for binding biomolecular analyte, i.e., it can be used to assay biomolecular analyte, wherein biomolecular analyte can comprise one or more of a variety of different biomolecules. In such embodiments, biomolecular analyte is deposited on the array, and the array is analyzed to determine the regions in which the biomolecular analyte exhibits a binding affinity. In some such embodiments, the biomolecules and biomolecular analyte are removed by treatment with proteinase K, wherein the proteinase K serves to catalyze hydrolytic fragmentation of proteins bound to the patterned OEG monolayer surface to regenerate the pattern. Biomolecular analyte suitable for such analysis (including sequencing) include, but are not limited to, oligonucleotides, proteins, and combinations thereof. In some or other embodiments, such an array is useful for screening drug candidates.

Figure 2:
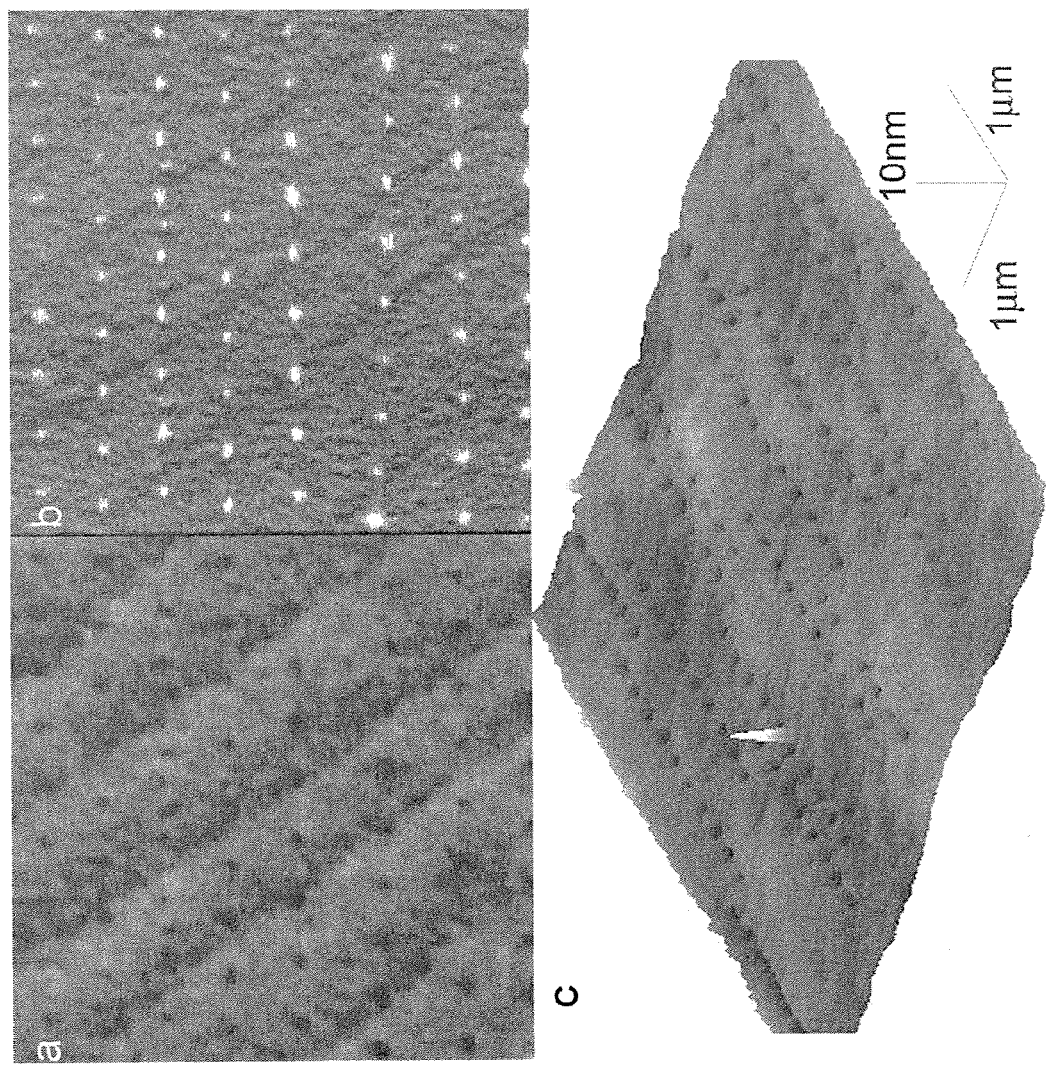
FIG. 2 depicts height ($2a$, $0.5 \times 0.5 \, \mu m^2$, 10 nm contrast) and friction ($2b$, 0.1 V contrast) AFM images of an $EG_7$ film on Si (111) after AFM anonization lithography, and a 3-dimensional image ($2c$, $5 \times 5 \, \mu m^2$) of a patterned area upon treatment with succinic anhydride, DMAP and pyridine.

The monolayers described herein can be readily prepared from □-hepta-(ethylene glycol) methyl ω-undecenyl ether, comprising seven EG ($EG_7$) repeat units (the term "$EG_7$" being used herein to describe both the repeat units and the alkene precursor comprising the seven EG repeat units), and conductive silicon (111) substrates with an atomically-flat, H-terminated surface (Yam et al., Chem. Commun., 2004, p. 2510). In accordance with some embodiments, AFM anodization lithography on these monolayers was performed under ambient conditions with a relative humidity of ~20-80%, using a Nanoscope IIIa AFM (Digital Instrument) equipped with a pulse generator. During AFM anodization on each location, a short pulse of +(4 to 17) V, with a duration typically in the range of about 10 nanoseconds (ns) to about 10 microseconds, was applied to the sample while the tip was grounded. During AFM anodization, the AFM scanner can rapidly position the AFM tip on the sample with nanometer precision. This process for generating a high-density nanoarray proved to be much faster than dip-pen or nanografting lithography techniques that normally take seconds to generate each nanospot. The pulse generator was then disconnected, and height and friction AFM images were simultaneously acquired in contact mode at a 90° scan angle with the same tip. In one specific example, in which the nanolithography was performed with 100 ns pulses of +10 V, it was found that holes with an apparent depth of 0.4 nm (corresponding to the length of one ethylene glycol unit) were generated, as revealed by the height images of the patterned areas, e.g., FIG. 2a. However, the corresponding friction image (FIG. 2b) shows the presence of spots of ~10 nm in diameter where the friction is higher than the surroundings, indicating the presence of polar head groups on the spots. Referring to FIG. 2, the spacing between the spots was ~50 nm, as controlled by the scanner.

While not intending to be bound by theory, it has been suggested that AFM anodization of alkyl siloxane monolayers on silicon under certain conditions could oxidize the head groups of the monolayers into carboxylic (COOH) groups [Maoz et al., J. Adv. Mater. 2000, v. 12, p. 725]. However, a recent study of a similar system using secondary ion mass spectroscopy showed no signs of COOH groups on the oxidized surfaces [Pignataro et al., Mater. Sci. Eng. C. 2003, v. 23, p. 7].

Figure 3:
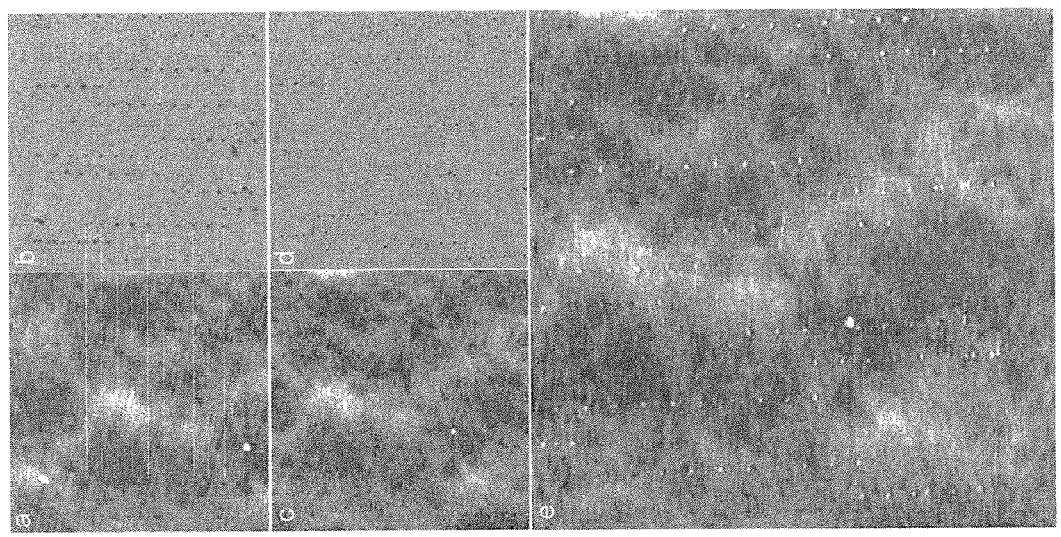
FIG. 3 depicts AFM height ($3a$, $3c$, and $3e$) and friction ($3b$ and $3d$, corresponding to $3a$ and $3c$) images ($4 \times 4 \, \mu m^2$) of an area similar to that shown in FIG. $2c$ upon sequential treatment with EDAC/avidin ($3a$-$b$), biotinylated-BSA ($3c$-$d$), and avidin ($3e$), wherein the lines in $3a$-$b$ are used as guides.

It should be noted that the monolayers in the above-described study had alkyl head groups, while the monolayers of the present invention comprise an OEG head group. The AFM anodization of the OEG-coated surfaces could be substantially different from the above-described alkyl surfaces. Preliminary studies by Applicants indicate that, upon AFM anodization of OEG-coated surfaces, a variety of species including carboxylic acids, aldehydes, and alcohols, are generated on the film surface. Additionally, in some embodiments, treatment of an AFM-anodized monolayer with avidin is done in the presence of 1-ethyl-3-(3-dimethylaminopropyl)-carbodiimide (EDAC, which serves to mediate the formation of amide bonds between the surface COOH groups and the protein molecules). Corresponding AFM images obtained during the first few scans showed that the protein molecules predominately adsorbed on the patterned spots. The protein molecules were readily removed by the scanning tip afterwards indicating that the protein molecules were not covalently bound to the surface. Again, while not intending to be bound by theory, it was concluded that rather than COOH groups, the surfaces of the oxidized spots mainly comprised hydroxyl groups that could be chemically converted into COOH groups, e.g., by treatment with succinic anhydride, dimethyl-aminopyridine (DMAP) and pyridine. Patterned spots were "etched" upon this treatment forming nanoholes as shown by the three-dimensional AFM height image (FIG. 2c). As measured by the line profile of about 100 patterned spots in FIG. 2c, the diameter of the holes was 91±6 nm, and the depth was 1.31±0.12 nm, about one third of the thickness of the film. Using the method described herein, COOH groups were generated in the nanoholes, which may be used to attach proteins. Upon incubation of the samples with EDAC followed by avidin in PBS solution, the nanoholes were nearly filled (FIG. 3a) and barely recognized even by comparison with the corresponding friction image (FIG. 3b). The depth of the holes decreased to 0.43±0.06 mm, while the width of the holes remained nearly the same (87±9 nm).

The sample was then treated with BSA in PBS buffer. The depth of the holes remained the same, indicating that BSA did not bind to the molecules in the holes. To verify that the molecules in the holes were indeed avidin, the sample was treated with a solution of biotinated-BSA in PBS buffer. AFM height and friction images (FIGS. 3c and 3d) reveal that the patterned spots protrude slightly from the film surface. The height and half-height width of the spots were 0.14±0.14 nm and 24±3.5 nm, respectively. The fact that the molecules in the holes bound biotinated-BSA but not native BSA is a strong indication that these molecules were avidin.

Figure 4:
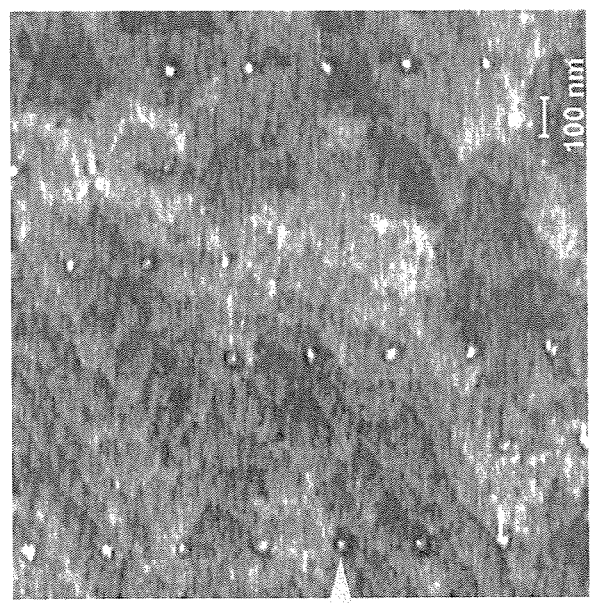
FIG. 4 demonstrates, schematically, a nanofabrication process, in accordance with embodiments of the present invention.
Figure 4:
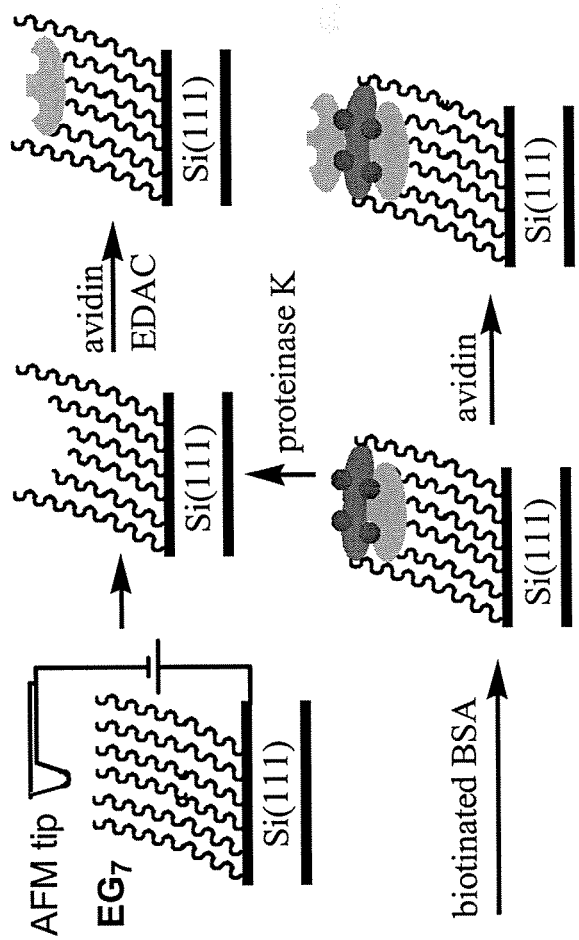

The patterned biotinated-BSA, with an average of nine biotin groups on each BSA molecule, should have free biotin groups available for binding additional avidin onto the pattern. Indeed, upon incubation of the sample in a solution of avidin in PBS, nano-dots arrays were formed, as shown by the AFM height image (FIG. 3e). The heights of the dots were 1.27±0.37 nm and the half-height widths of the dots were 26±3.4 nm. While the top avidin molecules could be removed by repeated scanning, the protein molecules in the holes were strongly bound, and could not be removed by the scanning tip, neither by immersion in PBS for 6 hours nor in detergent (SDS) solutions for 14 hours. AFM images of the protein arrays remained nearly the same after four weeks under ambient conditions. Upon treatment with Proteinase K (to catalyze the hydrolytic fragmentation of the proteins), nanoholes very similar to those in FIG. 2c were regenerated. The nanofabrication process, in accordance with some embodiments of the present invention, is demonstrated in FIG. 4.

Nanometric biomolecular array fabrication, as described herein and in accordance with embodiments of the present invention, will vastly improve the detection sensitivity (down to a single molecule), greatly facilitate single molecule sequencing of DNA, and serve as a powerful research tool for studying the cooperative interaction among multiple biomolecules.

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Example 1

This example serves to illustrate materials used in the fabrication of nanometric protein arrays, on protein-resistant monolayers on silicon surfaces, in accordance with embodiments of the present invention.

Pyridine, succinic anhydride, 4-dimethylaminopyridine (DMAP), 1-ethyl-3-(3-dimethylaminopropyl)-carbodiimide (EDAC), avidin, bovine serum albumin (BSA), biotinamidocaproyl labeled BSA (biotin-BSA), proteinase K, and phosphate buffered saline (PBS buffer, 0.01 M phosphate, 0.14 M NaCl, pH 7.4) were purchased and were used without purification.

Example 2

This example serves to illustrate the synthesis of hepta (ethylene glycol) methyl ω-undecenyl ether (comprising $EG_7$), as used in some embodiments of the present invention.

Monomethyl hepta(ethylene glycol) (1.637 g, 4.81 mmol) was slowly added to NaH (0.81 g, 33.75 mmol) in dry THF (8 ml) while stirring under $N_2$. To this mixture was added $Bu_4NI$ (0.81 g, 0.48 mmol) and 11-bromo-1-undecene (4.2 ml, 16.78 mmol), and the mixture was refluxed for 20 hours under $N_2$. Iodomethane (3.42 g, 24.1 mmol) was added, and the mixture was refluxed for 1 hour. The reaction mixture was then refluxed with methanol for another hour. After cooling to room temperature, the mixture was concentrated under reduced pressure. Dichloromethane was added, and the mixture was subsequently poured into water. The organic layer was separated, and the aqueous layer was extracted twice with dichloromethane. The combined organic layers were washed twice with water, dried with magnesium sulfate, filtered and concentrated under reduced pressure. The crude product was purified by flash chromatography (ethyl acetate/hexane/methanol 50:48:2) to afford $EG_7$ (1.8 g, 76%). $^1$H NMR ($CDCl_3$): δ=5.80-5.82 (m, 1H); 4.90-5.01 (m, 2H); 3.52-3.65 (m, 26H); 3.41-3.46 (t, 2H); 3.37 (s, 3H); 2.02-2.04 (q, 2H); 1.54-1.57 (m, 4H); 1.30-1.36 (m, 12H). $^{13}$C NMR ($CDCl_3$): δ=139.35, 114.22, 72.06, 71.67, 70.70, 70.65, 70.18, 59.17, 33.93, 29.76, 29.67, 29.60, 29.55, 29.25, 29.05, 26.21. ESI-MS: 516.5 (100%, M+I+$Na^+$).

Example 3

This example serves to illustrate photo-induced surface hydrosilylation, in accordance with embodiments of the present invention.

H-terminated silicon (100 or 111) surfaces were prepared using procedures similar to those described by Hines and Chidsey [Krämer et al., Chem. Rev. 2003, vol. 103, p. 4367]. Briefly, single-sided polished silicon (100) or silicon (111) wafers with a resistivity less than 5 ohm·cm were cut into pieces of ca. 1×1 $cm^2$, cleaned with $NH_4OH/H_2O_2/H_2O$ (v/v 1:1:4) at 80° C. for 20 minutes, thoroughly washed with Millipore-purified water, etched in 10% buffer-HF for 10 minutes and then in 40% $NH_4F$ for 10 minutes under $N_2$ purge, and dried with a flow of nitrogen. The setup and procedures for photo-induced surface hydrosilylation of H-terminated silicon substrate surfaces with alkenes were described in detail elsewhere [Yam et al., Chem. Commun., 2004, p. 2510]. Briefly, a freshly prepared H—Si (100) or H—Si (111) substrate was placed inside a freshly cleaned and dried quartz cell, and tilted with the polished surface facing a droplet (~1 mg) of the alkene ($EG_7$) that was placed on a surface in the cell. After the cell was degassed at ~0.1 mTorr for 10 minutes, the wafer was allowed to fall down onto the droplet, sandwiching a thin and homogeneous layer of the alkene between the substrate and the quartz wall. The substrate was then illuminated with a hand-held 254 nm UV lamp (Model UVLS-28, UVP) for 30 minutes, followed by washing sequentially with petroleum ether, ethanol, and $CH_2Cl_2$, and finally drying with a stream of $N_2$.

Example 4

This example serves to illustrate how Si surface type can affect the stability of the resulting nanometric biomolecular array.

Resistance comparisons between the adsorption and stability of OEG-terminated thin films on H—Si (100) and Si (111) were performed using the method as described in the present invention. Results indicated that the films of □-hepta(ethylene glycol) methyl ω-undecenyl ether, $EG_7$, on Si (111) and (100) substrates reduced adsorption of protein (fibrinogen) by >99%. The films were stable under a wide range of conditions, such as in biological buffers at pH 7.4 and 9.0 (37° C.), water (100° C.), and 2.5 M $H_2SO_4$(100° C.). The films derived on Si (111) were more stable than those on Si (100). Furthermore, it was demonstrated that the films on Si (100) or Si (111) could be patterned by AFM anodization lithography by the method as described in the present invention. The resultant patterns may serve as templates for directing the self-assembly of biomolecules such as fibrinogen, avidin, and bovine serum albumin (BSA) on the surfaces. See Yam et al., J. Colloid Interface Sci., 2005, in press.

Example 5

This example serves to illustrate AFM anodization lithography on $EG_7$-coated Si (100) or Si (111) substrates, in accordance with embodiments of the present invention.

Figure 5:
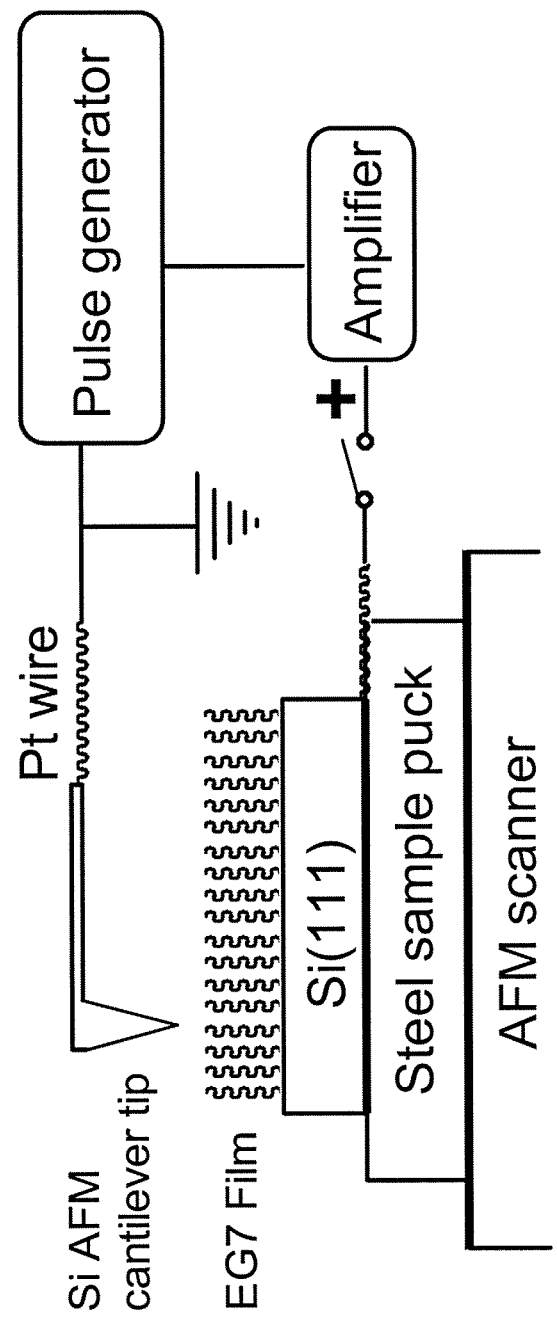
FIG. 5 illustrates a setup for AFM anodization lithography, in accordance with embodiments of the present invention.
Figure 6:
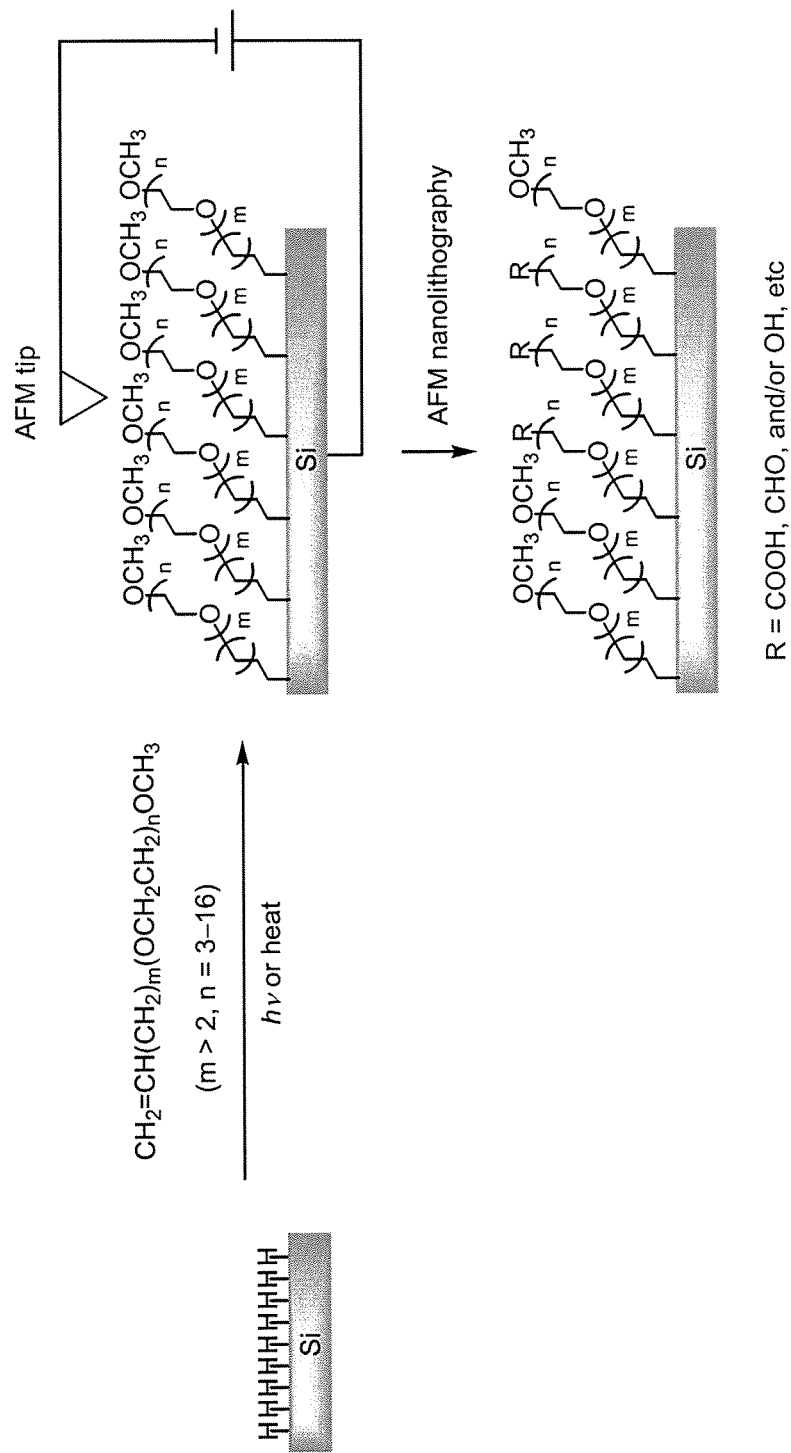
FIG. 6 illustrates AFM anodization lithography of an OEG monolayer on a Si surface, wherein the patterned (anodized) regions comprise functional moieties such as carboxylic acid, aldehyde, and/or alcohol, etc.

A setup for performing AFM anodization lithography on $EG_7$-coated Si (100) or Si (111) substrates, in accordance with embodiments of the present invention, is illustrated in FIG. 5. An OEG-coated silicon (100) or silicon (111) wafer was mounted on a steel sample puck using a double-sided carbon conductive tape that was also used to attach a short, thin Pt wire (25 μm in diameter). Another short, thin Pt wire was connected to the metal clip of a tip holder. The use of thin wires for electrical connection to the wafer and tip greatly reduces the vibration introduced to the system. Both Pt wires were connected through a BNC cable to a digital delay/pulse generator equipped with a homemade amplifier. The steel sample puck was mounted onto the AFM scanner that was insulated with a thin parafilm. AFM anodization lithograpy was performed under ambient conditions with a relative humidity of 25-55%, using a silicon cantilever with a force constant of 0.3 N/m and resistivity of ~0.08 ohm·cm. During scanning of the sample in contact mode (load: ~1 nN; scan size: 5×5 μm; scan rate: 29.8 μm/s), bursts of 10 pulses of +17 V square waves (pulse duration: 1 μs; interval between two pulses: 8.33 ms; interval between two bursts: 4.29 seconds) were applied to the sample while the tip was grounded. The nanolithography was completed in one scan, taking 85 seconds. For relocation of the nanopatterned areas after subsequent ex situ treatment of the sample, a tiny X mark with a line width of ~8 μm was drawn on the substrate with a diamond pen before nanolithgraphy, and the position of the cantilever relative to the mark shown by the CCD camera of the AFM was recorded. FIG. 6 illustrates the above-described AFM anodization lithography of an OEG monolayer on a Si surface, wherein the patterned (anodized) regions comprise carboxylic acid moieties.

Example 6

This example serves to illustrate AFM imaging, in accordance with embodiments of the present invention.

After nanolithography, the pulse generator was disconnected, and topography and friction AFM images were simultaneously acquired in contact mode at 90° scan angle with the same tip used for nanolithography. For imaging protein-coated surfaces, a soft cantilever with a force constant of 0.03 N/m was used at a loading force of ~1 nN.

Example 7

This example serves to illustrate derivatization of the nanoarrays with biomolecules, in accordance with embodiments of the present invention.

The patterned substrates were treated sequentially with (a) a solution of succinic anhydride (100 mg), and DMAP (12 mg) in pyridine (1 ml) for 30 minutes; (b) a solution of EDAC (1 mg) and avidin (0.1 mg) in PBS (1 ml) for 5 minutes; (c) BSA (1 mg) in PBS (1 ml) for 5 minutes; (d) biotin-BSA (1 mg) in PBS (1 ml) for 5 minutes; (e) avidin (0.1 mg) in PBS (1 ml) for 5 minutes; and (f) proteinase K (1 mg) in PBS (1 ml) for 3 hours. All treatments were carried out under ambient conditions. After each step, the substrates were thoroughly washed with Millipore water, dried with a stream of $N_2$, and immediately imaged by AFM.

Further Examples

Biocompatibility and Stability Study of OEG Films on Silicon

Protein-resistant thin films have been a subject of extensive research. Among many types of protein-resistant thin films, those presenting poly- or oligo(ethylene glycol) (PEG or OEG) deposited on various substrates, such as gold and silicon oxide, have been most extensively studied, and remain the most protein-resistant materials. [Vermette, P.; Meagher, L. "Interactions of phospholipid- and poly(ethylene glycol)-modified surfaces with biological systems: relation to physico-chemical properties and mechanisms." Colloid Surf. B-Biointerfaces 2003, 28, 153-198. Chen, S. F.; Yu, F. C.; Yu, Q. M.; He, Y.; Jiang, S. Y. "Strong resistance of a thin crystalline layer of balanced charged groups to protein adsorption." Langmuir 2006, 22, 8186-8191. Ostuni, E.; Chapman, R. G.; Holmlin, R. E.; Takayama, S.; Whitesides, G. M. "A survey of structure-property relationships of surfaces that resist the adsorption of protein." Langmuir 2001, 17, 5605-5620. Prime, K. L.; Whitesides, G. M. "Self-Assembled Organic Monolayers—Model Systems for Studying Adsorption of Proteins at Surfaces." Science 1991, 252, 1164-1167.] Applicant has developed a practical method to prepare OEG-presenting monolayers on silicon by surface hydrosilylation using the OEG-terminated alkenes (1, FIG. 7) and hydrogen-terminated silicon surfaces under UV illumination. [Yam, C. M.; Lopez-Romero, J. M.; Gu, J. H.; Cai, C. Z. "Protein-resistant monolayers prepared by hydrosilylation of alpha-oligo(ethylene glycol)-omega-alkenes on hydrogen-terminated silicon (111) surfaces." Chem. Commun. 2004, 2510-2511.] In the resulting monolayers the molecules are bound to the silicon surface through Si—C bonds. Through extensive optimization of the hydrosilylation process as well as the apparatus, the stability of these OEG-terminated monolayers and their ability to resist non-specific adsorption of proteins were greatly enhanced. The results are summarized in Table 1. Remarkably, the films remained to be highly resistant to protein adsorption after 4 weeks in PBS buffer at 37° C. To our knowledge, these films exhibit the highest stability among protein-resisting monolayers reported to date. Furthermore, the monolayers absorbed less than 3% monolayer of proteins in cell culture for 17 days, also representing the most protein-resistant monolayers reported to date.

TABLE 1

Protein-resistance* of OEG-terminated Monolayers on Silicon After Subjected to Various Conditions over Various Periods of Time

| Conditions | Time (days) | Adsorption of protein (% monolayer)** |
|---|---|---|
| Freshly-made films | 0 | 0 |
| PBS buffer at 37° C. | 28 | 0.5 |
| Freshly-made films tested with serum at D1 cell culture at 37° C. | 0 | 0 |
|  | 7 | 1.2 |
| MC3T3 cell culture at 37° C. | 17 | 2.8 |

*Expressed as the percentage of monolayer of fibrinogen absorbed on the sample after 1 h in 1 mg/mL fibrinogen solution, measured by $N_{OEG}/N_{Si-H} \times 100$ (%) where $N_{OEG}$ and $N_{Si-H}$ are the XPS N 1 s photoelectron signal intensity of the protein on the OEG films and H—Si(111) surface, respectively. The ellipsometric thickness of fibrinogen films on H—Si (111) surface is 6 nm, corresponding to a monolayer of the protein. [Yam, C. M.; Lopez-Romero, J. M.; Gu, J. H.; Cai, C. Z. "Protein-resistant monolayers prepared by hydrosilylation of alpha-oligo(ethylene glycol)-omega-alkenes on hydrogen-terminated silicon (111) surfaces." Chem. Commun. 2004, 2510-2511.]
**The standard deviations are 15% of the values, since we did not control the substrate orientation during XPS measurement. Wallart, X.; de Villeneuve, C. H.; Allongue, P. "Truly quantitative XPS characterization of organic monolayers on silicon: Study of alkyl and alkoxy monolayers on H—Si(111)." J. Am. Chem. Soc. 2005, 127, 7871-7878.

Click Reactions on the Surfaces

To allow highly specific interactions of the monolayers on silicon with biomolecular targets, we need to incorporate handles on the films for tethering the molecular probes. Although a variety of surfaces functional groups have been introduced to monolayers grown by hydrosilylation on silicon surfaces, [Buriak, J. M. "Organometallic chemistry on silicon and germanium surfaces." Chem. Rev. 2002, 102, 1271-1308.] incorporation of functional groups to allow 1,3-dipolar cycloaddition of terminal alkynes and azides ("click reaction") Kolb, H. C.; Finn, M. G.; Sharpless, K. B. "Click chemistry: Diverse chemical function from a few good reactions." Angew. Chem.-Int. Edit. 2001, 40, 2004-2021. has not been demonstrated. Click reaction is particularly suitable for bioconjugation since it usually gives high yields under physiological conditions, and is compatible with a wide range of functional groups and biomolecules. [Kolb, H. C.; Finn, M. G.; Sharpless, K. B. "Click chemistry: Diverse chemical function from a few good reactions." Angew. Chem.-Int. Edit. 2001, 40, 2004-2021. Brennan, J. L.; Hatzakis, N. S.; Tshikhudo, T. R.; Dirvianskyte, N.; Razumas, V.; Patkar, S.; Vind, J.; Svendsen, A.; Nolte, R. J. M.; Rowan, A. E.; Brust, M. "Bionanoconjugation via click chemistry: The creation of functional hybrids of lipases and gold nanoparticles." Bioconjugate Chem. 2006, 17, 1373-1375. Lee, J. K.; Chi, Y. S.; Choi, I. S. "Reactivity of acetylenyl-terminated self-assembled monolayers on gold: Triazole formation." Langmuir 2004, 20, 3844-3847. Lin, P. C.; Ueng, S. H.; Tseng, M. C.; Ko, J. L.; Huang, K. T.; Yu, S. C.; Adak, A. K.; Chen, Y. J.; Lin, C. C. "Site-specific protein modification through Cu—I-catalyzed 1,2,3-triazole formation and its implementation in protein microarray fabrication." Angew. Chem.-Int. Edit. 2006, 45, 4286-4290. Rostovtsev, V. V.; Green, L. G.; Fokin, V. V.; Sharpless, K. B. "A stepwise Huisgen cycloaddition process: Copper(I)-catalyzed regioselective "ligation" of azides and terminal alkynes." Angew. Chem.-Int. Edit. 2002, 41, 2596-2599. Sun, X. L.; Stabler, C. L.; Cazalis, C. S.; Chaikof, E. L. "Carbohydrate and protein immobilization onto solid surfaces by sequential Diels-Alder and azide-alkyne cycloadditions." Bioconjugate Chem. 2006, 17, 52-57. Tornoe, C. W.; Christensen, C.; Meldal, M. "Peptidotriazoles on solid phase: [1,2,3]-triazoles by regiospecific copper(I)-catalyzed 1,3-dipolar cycloadditions of terminal alkynes to azides." J. Org. Chem. 2002, 67, 3057-3064. Wang, Q.; Chan, T. R.; Hilgraf, R.; Fokin, V. V.; Sharpless, K. B.; Finn, M. G. "Bioconjugation by copper(I)-catalyzed azide-alkyne [3+2]cycloaddition." J. Am. Chem. Soc. 2003, 125, 3192-3193. To introduce the alkynyl groups to the surfaces, we employed the OEG-alkene terminated with a trimethylsilyl protected ethynyl group (2, FIG. 7) to prepare mixed monolayers with the matrix molecule 1 by hydrosilylation on H—Si(111) surfaces under UV illumination. To demonstrate the presence of ethynyl groups on the surface, we performed click reaction on the mixed monolayers using the azide 3 tethering a perfluorooctyl chain. XPS showed a strong F 1s signal upon this reaction but no F 1s signal upon subjecting the above films to the same conditions except the absence of 3. This result suggests the presence of ethynyl groups that could undergo click reactions.

Figure 7:
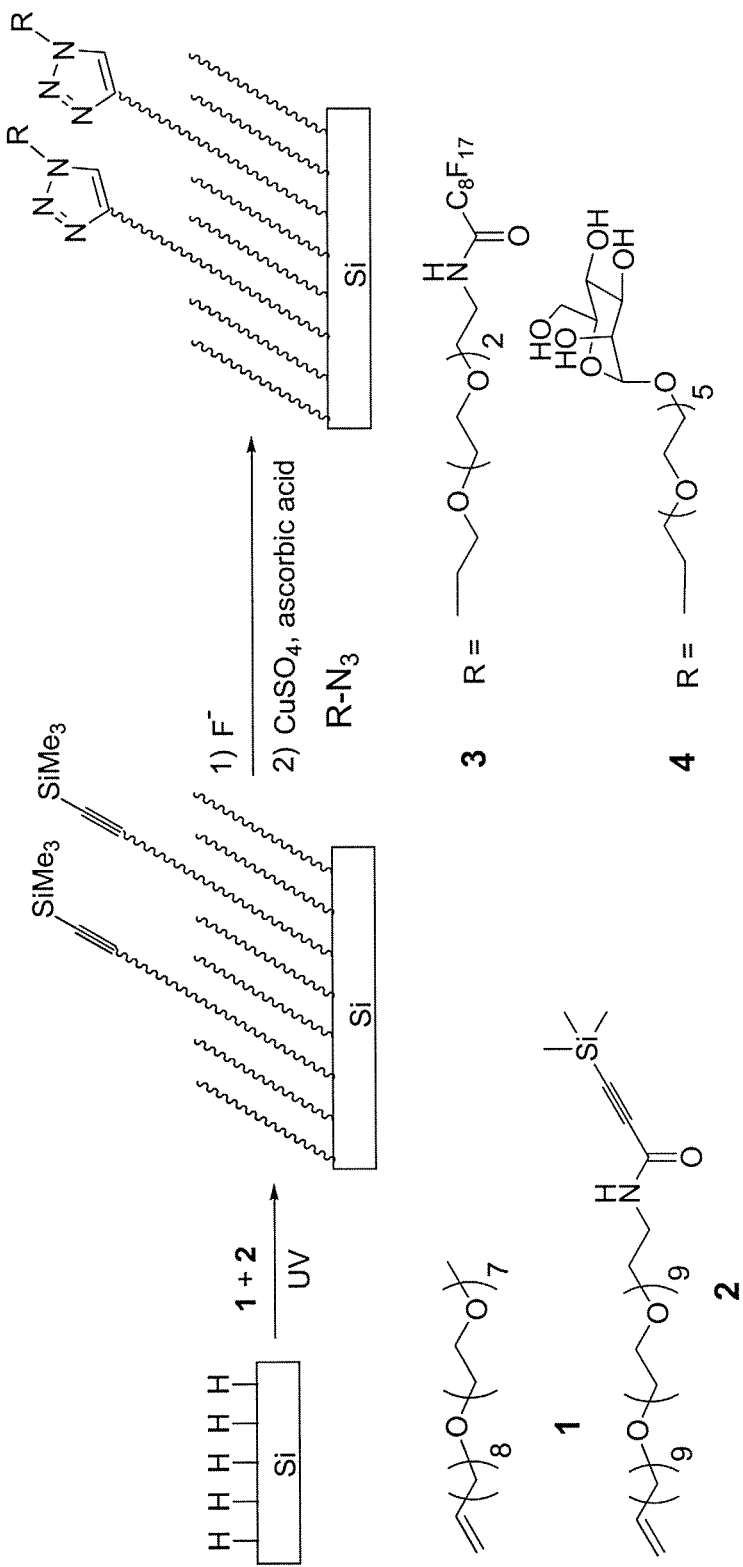
FIG. 7 shows a scheme for preparing OEG-presenting monolayers on silicon by surface hydrosilylation using the OEG-terminated alkenes.
Figures 8A, 8B:
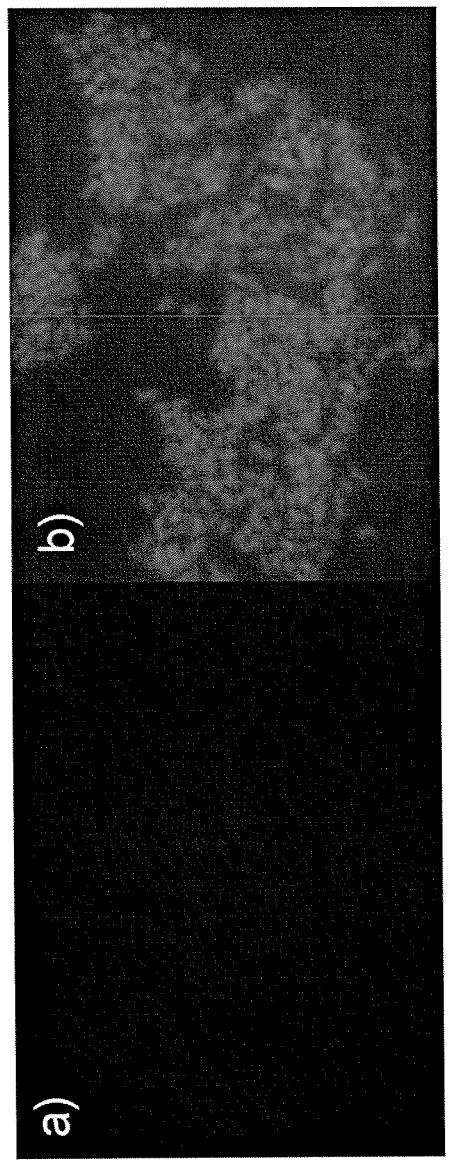
FIGS. 8$a$-$b$ show fluorescence image of an OEG (a) and a mannose-presenting monolayer (b) on silicon upon incubation with *E. coli* (strain 83972) followed by fixing with formaldehyde and staining with propidium iodide.

To demonstrate the potential biological applications of the ethynyl-presenting OEG surfaces on silicon substrates, we "clicked" mannose onto the surface using the azide 4 (FIG. 7). The bacteria used in the test were E. coli (strain 83972), E. coli (strain BL21) and Pseudomonas aeruginosa (strain 19660). All bacteria did not absorb on the OEG surfaces derived from 1 (FIG. 8a). The mannose-presenting surfaces could indeed capture E. coli (strain 83972) as shown by the fluorescence images (FIG. 8b), while it could not capture the other two bacteria that are lack of mannose acceptors.

Single Molecule Arrays for Study of Cell Responses

Several nanopatterning techniques have been developed for fabricating protein nanoarrays, including dip-pen nanolithography, nanografting, self-assembly of polymer micelles with a metallic core, and E-beam lithography. [Blattler, T.; Huwiler, C.; Ochsner, M.; Stadler, B.; Solak, H.; Voros, J.;

Grandin, H. M. "Nanopatterns with biological functions." *J. Nanosci. Nanotechnol.* 2006, 6, 2237-2264.] Alternatively, we have developed a method based on conductive AFM (cAFM) nanolithography on OEG-terminated monolayers on silicon. We have demonstrated the highest resolution (25 nm) for fabrication of protein nanoarrays on protein-resistant surfaces. Gu, J. H.; Yam, C. M.; Li, S.; Cai, C. Z. "Nanometric protein arrays on protein-resistant monolayers on silicon surfaces." *J. Am. Chem. Soc.* 2004, 126, 8098-8099.

Figure 9:
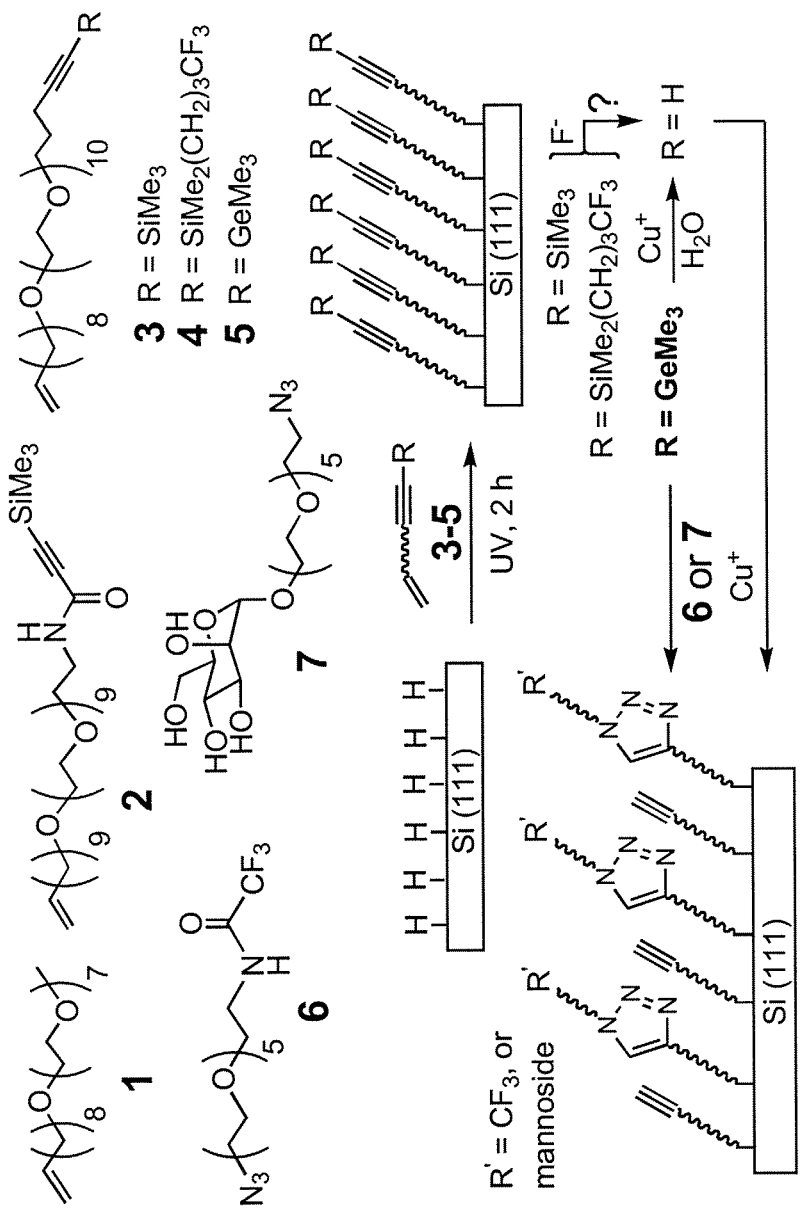
FIG. 9 shows a scheme for derivitizing C≡C-TMG groups.

To gain insights of the cell responses to nanoscale presentation of signaling molecules, we are developing a methodology to precisely control the location and number of ligands on the surface as shown in FIG. 9. Briefly, nanotemplates presenting carboxylic acid groups are generated on OEG-terminated surfaces by cAFM, which employs a bias voltage to induce local electrochemical oxidation on the monolayer. The feature size of the pattern should be small enough to accommodate no more than one generation 5 polyamidoamine (PAMAM) molecule, which is partially coated with OEG and modified with a defined number of functional groups such as ethynyl or azido groups for click reactions. Upon amidation of the functionalized PAMAM on the nanotemplate, biomolecular probes can be tethered to the templates via click reactions.

To realize this concept, a crucial step is to reduce the feature size down to about 10 nm, which is similar to the size of one generation 5 PAMAM molecule spreading on polar surfaces. Through mechanistic study of the cAFM process using model compounds, we found that it is possible to selectively oxidize only the surfaces of the OEG monolayer, and the feature size of the generated patterns is determined by the size of water meniscus where hydroxy radicals are generated. After extensive optimization of the conditions for c-AFM, we successfully reduced the feature size down to about 10 nm.

We have demonstrated that OEG-terminated monolayers prepared by our method are among the most protein-resistant and stable monolayers reported to date. The films absorbed less than 3% monolayer of protein after 17 days in MC3T3 cell culture at 37° C., and remained protein-resistant even after 28 days in PBS buffer. We are collaborating with other groups to perform implantation of these OEG-coated silicon samples to study their in vivo biocompatibility and long-term stability. We also prepared mixed OEG-monolayers presenting ethynyl groups onto H—Si (111) surfaces, and introduced mannose groups onto the surface using click reactions. Finally, we showed that the mixed monolayers presenting mannose selectively captured *E. coli* that has mannose receptors. We will collaborate with other groups to fabricate demo devices using the above platforms for various biosensing applications.

In contribution to our effort to prepare single molecule arrays, after mechanistic studies and extensive optimization of the c-AFM nanopatterning on the OEG monolayers, we have successfully reduced the feature size down to ~10 nm, which could accommodate no more than one large PAMAM molecule on each spot. Future work will include demonstration of tethering of single PAMAM molecule onto each spot on the nanopattern and the use of these single molecule arrays to study cellular pattern-recognition.

Still Further Examples

Modification of silicon substrates with biomolecules is of tremendous interest for the development of silicon-based biodevices such as (implantable) biosensors and neuron interfaces. [Yang, W. S.; Butler, J. E.; Russell, J. N.; Hamers, R. J. *Analyst* 2007, 132, 296; K'Owino, I. O.; Sadik, O. A. *Electroanalysis* 2005, 17, 2101; Hochberg, L. R.; Serruya, M. D.; Friehs, G. M.; Mukand, J. A.; Saleh, M.; Caplan, A. H.; Branner, A.; Chen, D.; Penn, R. D.; Donoghue, J. P. *Nature* 2006, 442, 164.] Using silicon as the substrates for these applications has several unique advantages, including the availability of well-established micro-fabrication processes and electronic and mechanical properties. For these applications, it is often desirable to modify silicon surfaces to reduce inflammatory response that degrades their performance. To address this need, we have developed a practical technique [Cai, C.; Yam, C. M.; Xiao, Z.; Gu, J. Modification of silicon-containing scanning probe microscopy tips and growth of oligo- or poly(ethylene glycol) films on silicon surfaces through formation of Si—C bonds; U.S. Pat. No. 7,247,384; Yam, C. M.; Lopez-Romero, J. M.; Gu, J. H.; Cai, C. Z. *Chem. Commun.* 2004, 2510; Yam, C. M.; Gu, J.; Li, S.; Cai, C. *J. Colloid Interface Sci.* 2005, 285, 711.] for preparing highly protein-resistant and stable monolayers by hydrosilylation [Linford, M. R.; Fenter, P.; Eisenberger, P. M.; Chidsey, C. E. D. *J. Am. Chem. Soc.* 1995, 117, 3145; Buriak, J. M. *Chem. Rev.* 2002, 102, 1271.] of the alkene 1 on hydrogen-terminated silicon surfaces. The monolayers consist of an oligo (ethylene glycol) (OEG) layer on top of an ultrathin (13 Å), well-ordered, highly dielectric alkyl layer directly bound to the silicon surface. These monolayers are bound to the silicon surface via Si—C bonds with a high density, rendering them the most protein-resistant and stable monolayers reported to date. In addition, such ultrathin (~4 nm) monolayers on non-oxidized silicon are ideal interfaces for highly sensitive transduction of electrical and biological signals. To permit specific interactions with targeted biological entities, the monolayer surface needs to be functionalized with ligands. For this purpose, we are interested in the bioconjugation chemistry based on cycloaddition of acetylenes and azides ("click" reaction), since the chemistry is specific and compatible with a wide range of biomolecules under physiological conditions, [Rostovtsev, V. V.; Green, L. G.; Fokin, V. V.; Sharpless, K. B. *Angew. Chem. Int. Edit.* 2002, 41, 2596; Tomoe, C. W.; Christensen, C.; Meldal, M. *J. Org. Chem.* 2002, 67, 3057; Wu, P.; Fokin, V. V. *Aldrichimica Acta* 2007, 40, 7; Nandivada, H.; Jiang, X. W.; Lahann, *J. Adv. Mater.* 2007, 19, 2197; Agard, N. J.; Baskin, J. M.; Prescher, J. A.; Lo, A.; Bertozzi, C. R. *ACS Chem. Biol.* 2006, 1, 644; Lutz, J. F. *Angew. Chem. Int. Ed.* 2007, 46, 1018; Wang, Q.; Chittaborina, S.; Barnhill, H. N. *Lett. Org. Chem.* 2005, 2, 293; Binder, W. H.; Sachsenhofer, R. *Macromol. Rapid Commun.* 2007, 28, 15.] and it has been used to modify various types organic thin films. [Ciampi, S.; Bocking, T.; Kilian, K. A.; James, M.; Harper, J. B.; Gooding, J. J. *Langmuir* 2007, 23, 9320; Lin, P. C.; Ueng, S. H.; Yu, S. C.; Jan, M. D.; Adak, A. K.; Yu, C. C.; Lin, C. C. *Org. Lett.* 2007, 9, 2131; Lin, P.-C.; Ueng, S.-H.; Tseng, M.-C.; Ko, J.-L.; Huang, K.-T.; Yu, S.-C.; Adak, A. K.; Chen, Y.-J.; Lin, C.-C. *Angew. Chem. Int. Ed.* 2006, 45, 4286; Sun, X. L.; Stabler, C. L.; Cazalis, C. S.; Chaikof, E. L. *Bioconjugate Chem.* 2006, 17, 52; Zhang, Y.; Luo, S.; Tang, Y.; Yu, L.; Hou, K.-Y.; Cheng, J.-P.; Zeng, X.; Wang, P. G. *Anal. Chem.* 2006, 78, 2001; Duckworth, B. P.; Xu, J. H.; Taton, T. A.; Guo, A.; Distefano, M. D. *Bioconjugate Chem.* 2006, 17, 967; Lummerstorfer, T.; Hoffmann, H. *J. Phys. Chem. B* 2004, 108, 3963; Lee, J. K.; Chi, Y. S.; Choi, I. S. *Langmuir* 2004, 20, 3844; Gallant, N. D.; Layery, K. A.; Amis, E. J.; Becker, M. L. *Adv. Mater.* 2007, 19, 965; Collman, J. P.; Devaraj, N. K.; Eberspacher, T. P. A.; Chidsey, C. E. D. *Langmuir* 2006, 22, 2457; Fleming, D. A.; Thode, C. J.; Williams, M. E. *Chem. Mat.* 2006, 18, 2327; Rozkiewicz, D. I.; Janczewski, D.; Verboom, W.; Ravoo, B. J.; Reinhoudt, D. N. *Angew. Chem. Int. Ed.* 2006, 45, 5292; Devadoss, A.; Chidsey, C. E. D. *J.*

Am. Chem. Soc. 2007, 129, 5370; Bryan, M. C.; Fazio, F.; Lee, H.-K.; Huang, C.-Y.; Chang, A.; Best, M. D.; Calarese, D. A.; Blixt, O.; Paulson, J. C.; Burton, D.; Wilson, I. A.; Wong, C.-H. *J. Am. Chem. Soc.* 2004, 126, 8640; Rohde, R. D.; Agnew, H. D.; Yeo, W. S.; Bailey, R. C.; Heath, J. R. *J. Am. Chem. Soc.* 2006, 128, 9518; Prakash, S.; Long, T. M.; Selby, J. C.; Moore, J. S.; Shannon, M. A. *Anal. Chem.* 2007, 79, 1661; Nandivada, H.; Chen, H. Y.; Bondarenko, L.; Lahann, *J. Angew. Chem. Int. Ed.* 2006, 45, 3360; White, M. A.; Johnson, J. A.; Koberstein, J. T.; Turro, N. J. *J. Am. Chem. Soc.* 2006, 128, 11356; O'Reilly, R. K.; Joralemon, M. J.; Wooley, K. L.; Hawker, C. J. *Chem. Mat.* 2005, 17, 5976; Li, H. M.; Cheng, F. O.; Duft, A. M.; Adronov, A. *J. Am. Chem. Soc.* 2005, 127, 14518.] Herein, we report a method for incorporating acetylene derivatives onto well-defined, OEG-based monolayers on silicon substrates that allows direct tethering of biomolecules via click chemistry.

Click reactions have been implemented on various types of substrates, such as gold, [Collman, J. P.; Devaraj, N. K.; Chidsey, C. E. D. *Langmuir* 2004, 20, 1051; Collman, J. P.; Devaraj, N. K.; Eberspacher, T. P. A.; Chidsey, C. E. D. *Langmuir* 2006, 22, 2457; Lee, J. K.; Chi, Y. S.; Choi, I. S. *Langmuir* 2004, 20, 3844.] silicon oxide, [Lummerstorfer, T.; Hoffmann, H. *J. Phys. Chem. B* 2004, 108, 3963; Rozkiewicz, D. I.; Janczewski, D.; Verboom, W.; Ravoo, B. J.; Reinhoudt, D. N. *Angew. Chem. Int. Ed.* 2006, 45, 5292; Sun, X. L.; Stabler, C. L.; Cazalis, C. S.; Chaikof, E. L. *Bioconjugate Chem.* 2006, 17, 52.] graphite, [Senyange, S.; Anariba, F.; Bocian, D. F.; McCreery, R. L. *Langmuir* 2005, 21, 11105.] and porous silicon. [Bateman, J. E.; Eagling, R. D.; Worrall, D. R.; Horrocks, B. R.; Houlton, A. *Angew. Chem. Int. Ed.* 1998, 37, 2683.] Only a few examples were reported on non-oxidized silicon surfaces. [Hurley, P. T.; Ribbe, A. E.; Buriak, J. M. *J. Am. Chem. Soc.* 2003, 125, 11334; Rohde, R. D.; Agnew, H. D.; Yeo, W. S.; Bailey, R. C.; Heath, J. R. *J. Am. Chem. Soc.* 2006, 128, 9518; Clampi, S.; Bocking, T.; Kilian, K. A.; James, M.; Harper, J. B.; Gooding, J. J. *Langmuir* 2007, 23, 9320.] Direct bonding on non-oxidized silicon eliminates the dielectric silicon oxide layer, thus greatly improving the electrical communication with the silicon substrate.

Initially, we attempted to perform photo- or thermal-initiated hydrosilylation with alkenes terminated with an azido group on H—Si(111) surfaces, but failed, likely due to the instability of the azido groups under the deposition conditions. We then envisioned that ethynyl groups might survive the reaction conditions if they were protected with a bulky group such as trimethylsilyl (TMS) group. Although the propiolamide derivative 2 (FIG. 9) polymerized under UV, the non-conjugated alkyne 3 was stable and completed hydrosilylation on hydrogen-terminated Si(111) surfaces within 2 h under UV (254 nm). The resulting monolayers exhibited an ellipsometric thickness of 52.3±1.2 Å, close to the length (59 Å) of extended 3 calculated by MM2. The percentage of C—O moieties in the film was 56.5% (expected: 58%) as determined by X-ray photoelectron spectroscopy (XPS) by deconvoluting the C 1s signals at 286.7 eV (assigned to C—O) and at 285.0 eV (assigned to the rest C atoms).[2] However, the attempted desilylation followed by click reaction on the monolayers was not successful, probably because the removal of the TMS group was problematic (see below). To allow reliable monitoring of the deprotection step, we used a fluorated alkylsilyl group to protect the terminated alkyne as in 4. Surface hydrosilylation of 4 resulted in a film with an ellipsometric thickness of 60.5±0.9 Å, close to the calculated length (62 Å) of the extended 4. According to the XPS measurement, the (C—O) % in the film was 54.1% (expected: 54.9%), and the C/O/F ratio was 1:0.28:0.027, close to the expected value of 1:0.27:0.023. Removal of the fluorinated alkylsilyl group on the monolayer was monitored by the F 1s XPS signal. In contrast to the rapid desilylation (completed within 30 min) for compound 4 in THF solution of Bu$_4$NF (0.2 equiv.), desilylation of the monolayers derived from 4 in the same solution was sluggish, probably due to the combination of steric hindrance and hydrophobicity of the surface. Indeed, for the mixed monolayers prepared by co-deposition of 1 and 4 in a 10:1 ratio, the desilylation proceeded in a substantially higher rate, especially in the presence of Cu$^+$ that coordinates with C≡C and thus activates the nucleophilic attack on Si. Thus, the desilylation was completed in 40 min in a solution of Bu$_4$NF (0.3 mM) and CuOAc (0.03 mM) in THF. Unfortunately, under these conditions partial oxidation of the silicon interface also occurred, as shown by the appearance of the silicon oxide peak at 103 eV.

Figure 10B:
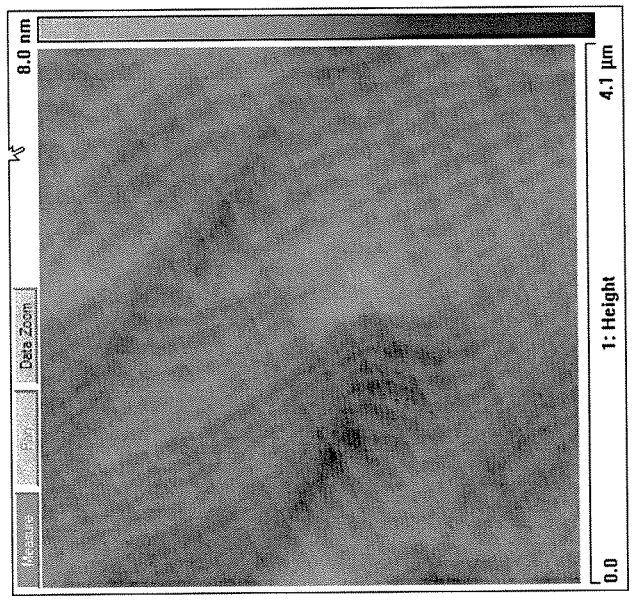
FIGS. 10$a$-$b$ shows tapping mode AFM images of the TMG-protected alkyne on Si (111) surface: (A) $7.0 \times 7.0 \, \mu m$; (B) $4.1 \times 4.1 \, \mu m$.
Figure 10A:
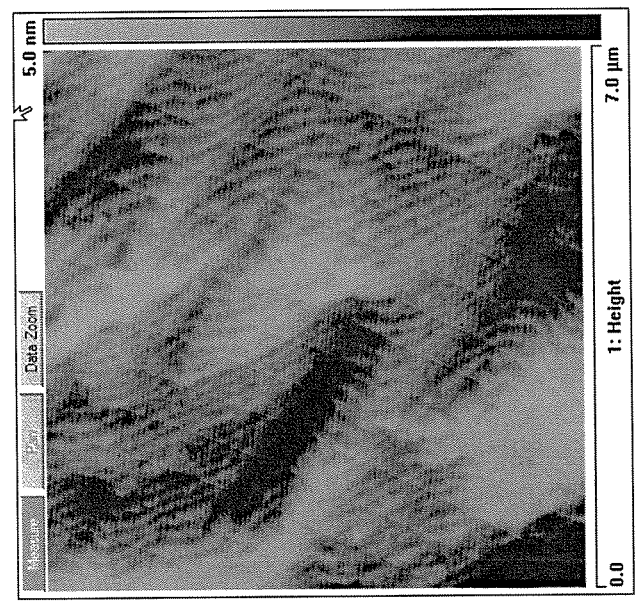

In search for a protecting group for terminal alkynes that could be removed under very mild, neutral conditions, we turned our attention to trimethylgermanyl (TMG) group. [Ernst, A.; Gobbi, L.; Vasella, A. *Tetrahedron Lett.* 1996, 37, 7959; Cai, C. Z.; Vasella, A. *Helv. Chim. Acta* 1995, 78, 732.] TMG group on terminal alkynes can be readily removed in protic solvents in the presence of catalytic amounts of Cu$^+$. The monolayer presenting C≡C-TMG groups was derived from the alkenyne 5 (FIG. 9). The ellipsometric thickness of the monolayer was 58.4±0.1 Å, close to the estimated length (59 Å) of the extended molecule, indicative of no hairpining of the alkyne molecule on the surface and that the observed film is indeed a monolayer thick. The result is further verified through the appearance of the underlying atomic steps of the silicon (111) substrate as shown on the AFM image, as shown in FIG. 10.

Figures 11A, 11B, 11C, 11D:
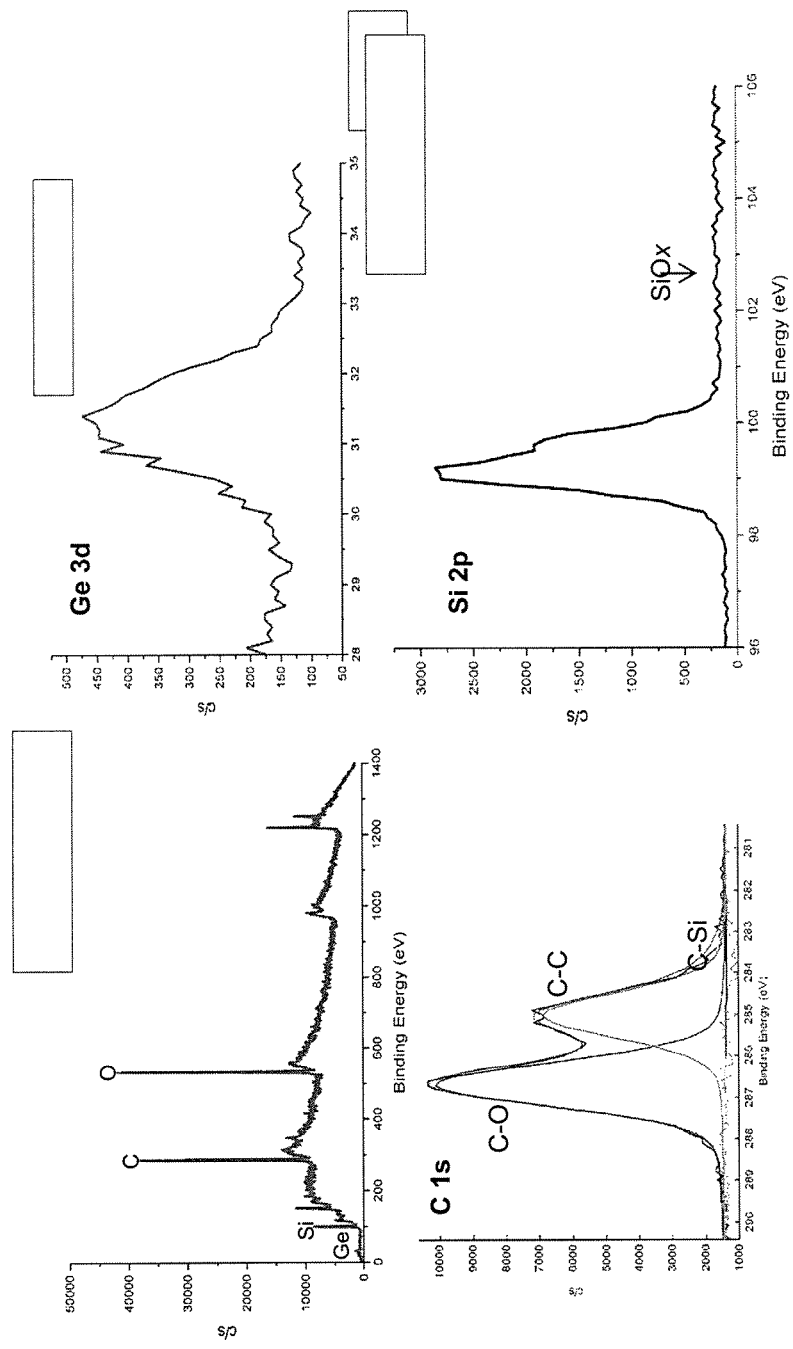
FIGS. 11$a$-$d$ show survey and high resolution spectra of the TMG-protected alkyne on Si (111): (A) Survey spectrum; (B) High resolution C1s scan; (C) High resolution Ge 3d scan; (D) High resolution Si 2p scan.

XPS spectra acquired on the TMG terminated monolayer are shown on FIG. 11. The survey spectra showed the presence of C, O, Ge and Si, as expected. High resolution scans of the Si 2p spectra showed the absence of peak at 101-104 eV regions suggesting no significant oxide or suboxide silicon was present. This result is also in accord with the observed formation of high density monolayer from the TMG-terminated alkene 5. XPS result on the Ge 3d region showed a strong peak at 30.1 eV, indicating the presence of the TMG group on the surface. An advantage of using TMG as the protecting group is that the Ge 3d signal can be used to estimate the density of the ethynyl groups on the surface, and the yield of the deprotection. The narrow scan in the C 1s region showed the presence of C—C, C—O peaks with a mean binding energy at 285.0 eV and 286.7 eV, respectively. The peaks were analyzed first by background subtraction using the Shirley routine and a subsequent non-linear fitting to mixed Gaussian-Lorentzian functions. The data from the C1s spectra were fitted to functions having 80% Gaussian and 20% Lorentzian character. A satellite peak shifted at a slightly lower binding energy (283.8 eV) was also assigned to contributions from C—Si. This is consistent with the expected result for a slightly negatively charged carbon atoms (Si—C—R$_1$, R$_2$, R$_3$; R$_1$, R$_2$, R$_3$≡C, H). Atomic concentration contributions were also determined from the XPS and the ratio of concentrations of C:O:Ge was found to be 1:0.30:0.029 and is close to the expected value of 1:0.29:0.026.

As expected, 95% of the TMG group on the monolayer was removed in 1 h in a solution of Cu(MeCN)$_4$PF$_6$ (10 mM) and ascorbic acid (50 mM) in methanol under nitrogen. The click reaction on the deprotected alkyne surface was tested using the fluoride-containing azide 6 (5 mM) and Cu(MeCN)$_4$PF$_6$ (10 mM) in methanol/ethanol/water (v/v/v 2:1:1) overnight. XPS showed the F 1s signal at 690 eV and N 1s signal at 401 eV, indicating the presence of the CF$_3$ group, and the triazole and amide groups, respectively. No signal was present at 405 eV corresponding to the central, electron-deficient N-atom in the azido group, indicating no physisorption of 6 in the film.

Figure 12:
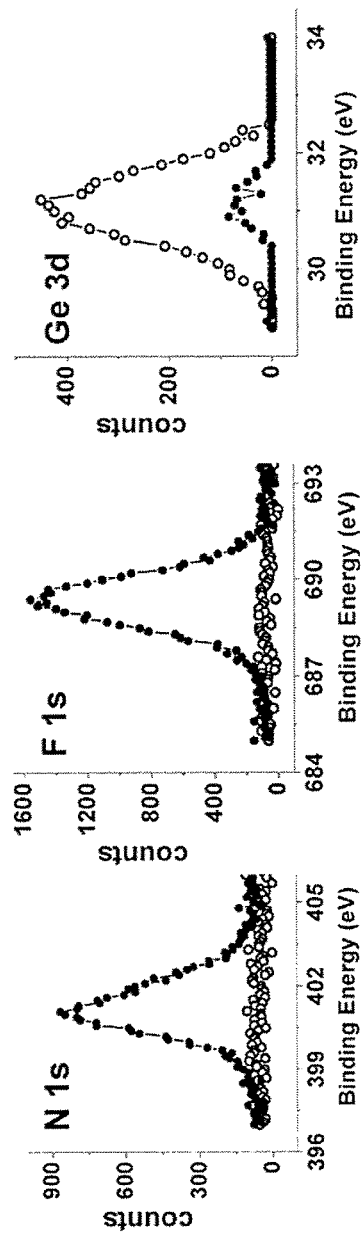
FIG. 12 shows N 1s, F 1s and Ge 3d region of XPS profile of films derived from 5 before (circle) and after (solid) click reaction with 6.

An additional advantage of using TMG protecting group is that the $Cu^+$-catalyzed deprotection proceeds faster than the click reaction under the same conditions. Hence, they can be combined into one step (Scheme 1). Indeed, XPS data showed that the monolayer presenting C≡C-TMG groups underwent click reaction with the azide 6 (5.0 mM) in the presence of $Cu(MeCN)_4PF_6$ (2.5 mM) and ascorbic acid (25.0 mM) overnight. The F 1s signal appeared at 690 eV and N 1s at 401 eV, accompanied by the reduction of the Ge 3d signal intensity by 95% (FIG. 12). The N 1s signal was deconvoluted and fitted to three peaks assigned to CONH (401.7 eV), N—N≡N (400.8 eV), and N—N≡N (400.1 eV); the ratio of the peak areas was about 1.2:2:1. Moreover, the N/F ratio was 1.31 (expected 1.33). Based on the C/F ratio (32.11) measured by XPS, the reaction yield was estimated to be 43%. The incomplete click reaction between the surface alkynes and the OEG-azide 6 in the solution remained unclear. It might have been due to the steric hindrance, or homo-coupling of the terminal alkynes in the presence of $Cu^+$ and adventitious $O_2$.

Figure 13:
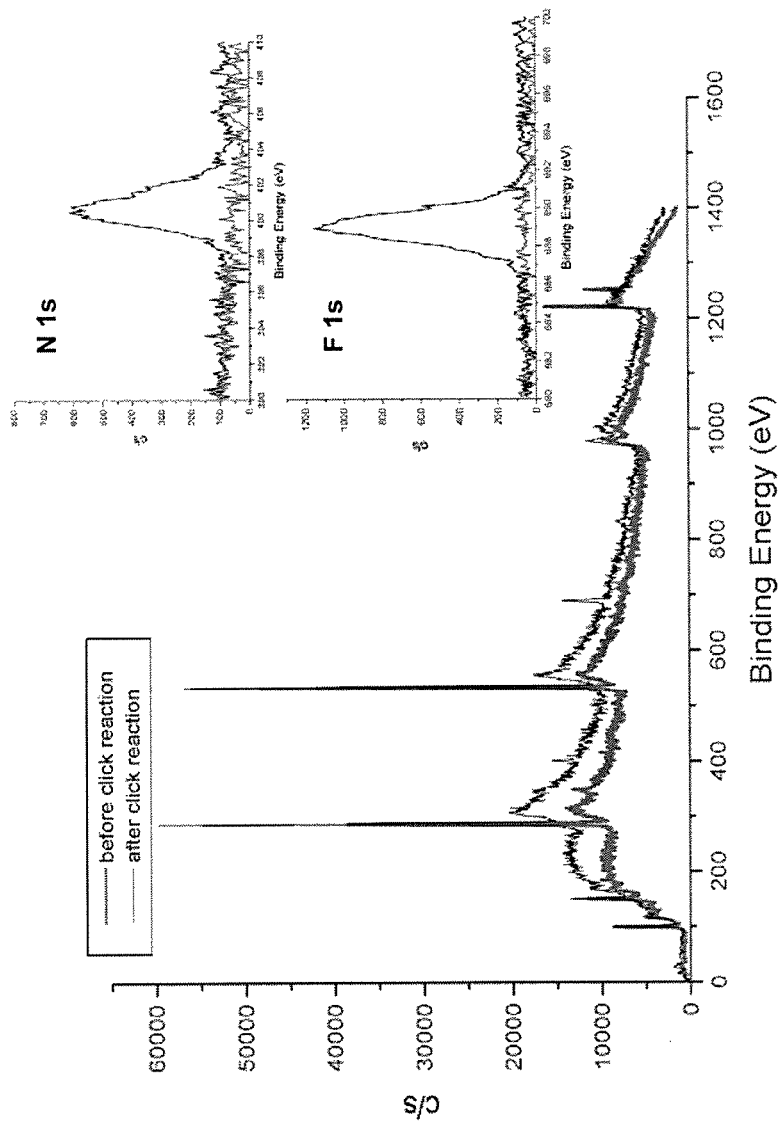
FIG. 13 shows survey and high resolution spectra before and after the surface click reaction on Si(111), wherein the inset shows high resolution scans on the F 1s and N 1s regions before and after the reaction.
Figures 14A, 14B:
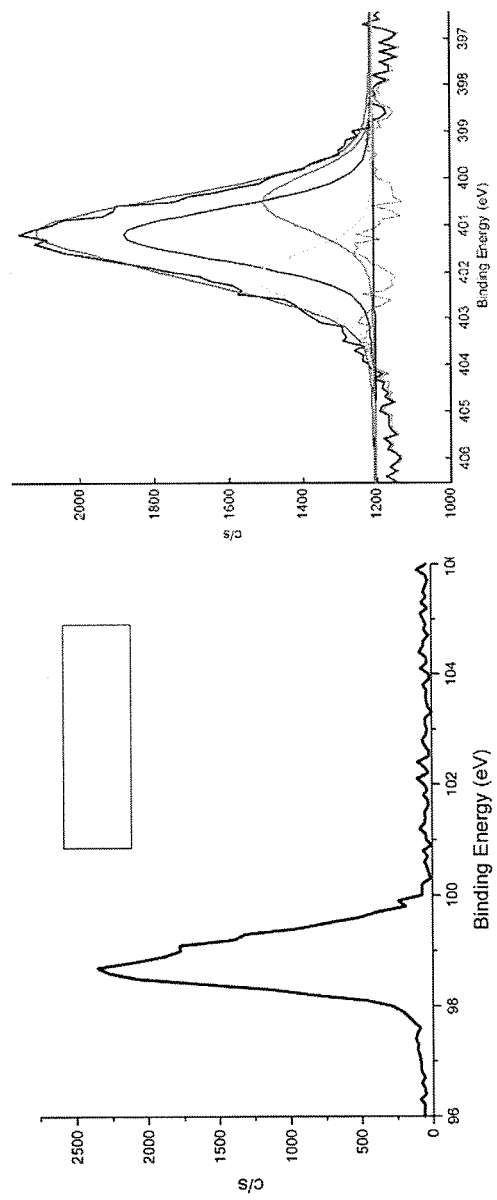
FIGS. 14$a$-$b$ show high resolution scans of the functionalized Si (111) surface after the click reaction: (A) Si 2p (B) N1.

Another example of surface click reaction is described below. In a reaction vial containing the alkyne terminated surface, 200 μL of the copper catalyst (5 mM) and ascorbic acid (50 mM) in methanol was added. The solution was allowed to stand for 10 minutes and was followed by the addition of the azide (10 mM in ethanol/water (1:1 v/v)). The cycloaddition reaction was allowed to proceed for 12 h under $N_2$ environment. FIG. 13 shows the XPS survey spectra and high resolution spectra before and after the click reaction. The survey spectra reveal the presence of the N1s and F1s signals, which were not observed before the click reaction. The strong peak at 690 eV from the F1s spectra suggests the presence of $CF_3$ group, while the high resolution N1s spectra provided evidence for the formation of triazole moeiety and thus the occurrence of click. Narrow scan of the Si 2p region showed no detectable levels of SiOx species in the 102-104 eV region (FIG. 14). The N1s spectra (FIG. 13) was deconvoluted and fitted into three peaks. The peaks were assigned as the amide nitrogen (402.1 eV), the double bonded nitrogen (401.2 eV) in the triazole ring and the singly bonded nitrogen (400.5 eV) in the ring. The ratio of the integrated peaks were found to be 1:2:1 and is consistent with the expected structure. Moreover, no peak was observed at ~405 eV, corresponding to the electron deficient nitrogen group in the azide group. This signifies the absence of any unreacted azide present in the monolayer.

Figure 15B:
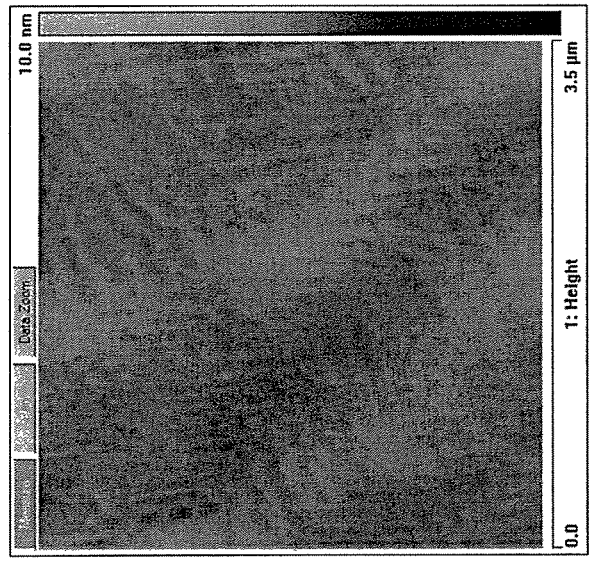
FIGS. 15$a$-$b$ show tapping mode AFM images of the resulting film after click reaction of the alkyne terminated Si(111) surface and the fluoride EG-6 functionalized azide: (A) $3.2 \times 3.2 \, \mu m$; (B) $3.5 \times 3.5 \, \mu m$.
Figure 15A:
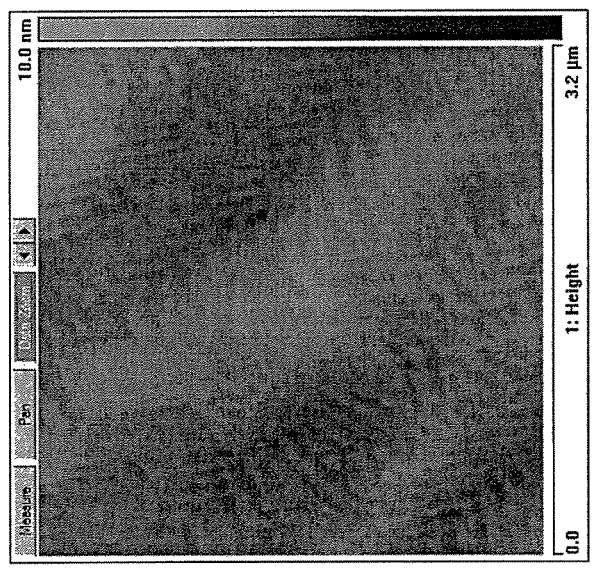

The topographies of the monolayer were observed using AFM (FIG. 15) and reveals a flat and homogeneous surface even after the coupling reaction. The Si (111) steps were also visible suggesting a monolayer formation. The occurrence of a monolayer after the click reaction was further verified with the observed increase in thickness. The thickness was found to be 68.4±0.4 Å which is close to its calculated thickness 70 Å.

Optimization of the Yields
The Influence of Oxygen

The CuAAC reactions were performed under different conditions with varied oxygen content. Two sets of experiments were performed and the general procedure mentioned with respect to FIG. 13 was followed. The results are summarized in Table 1. Higher yields were observed on anaerobic conditions and a significantly low yield for click systems ran without the exclusion of air (~22% versus ~53%). The results are attributed to the high sensitivity of $Cu^+$ towards oxidation by $O_2$ to form $Cu^{2+}$, even in the presence of ascorbic acid that reduces $Cu^{2+}$ back to $Cu^+$. Upon oxidation, the copper catalyst is deactivated and the resultant to $Cu^{2+}$ species promote the homocoupling of alkynes.

Figure 16:
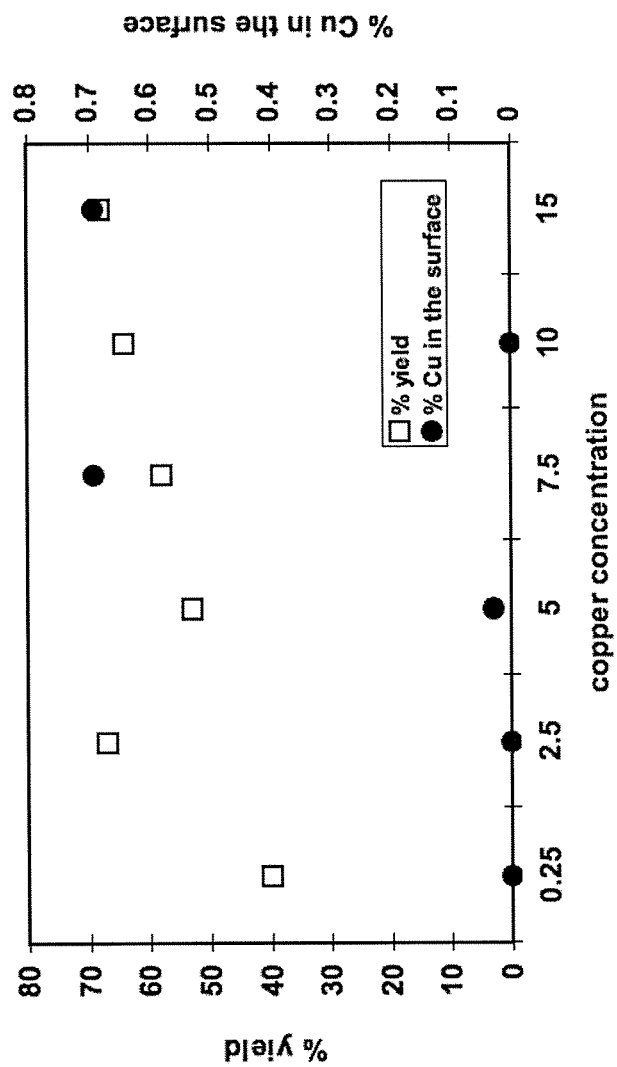
FIG. 16 shows The effect of varying concentration of copper catalyst on the percent conversion of the click reaction performed on Si (111)

Given that higher yields were observed for click reactions performed under anaerobic conditions, coupling reactions for all succeeding conditions were performed under anaerobic environment. Methanol, the solvent used for dissolving the catalyst was freeze-thawed several times (at least 6×) prior to each use. The rest of the conditions were kept constant, except that the concentration of the copper complex was varied. Referring to FIG. 16, conditions were: 200 μL $Cu(MeCN)_4PF_6$ (0.25, 2.5, 5, 7.5, 10, 15 mM) and ascorbic acid (50 mM) in methanol; 250 μL azide (10 mM) in ethanol/water (1:1 v/v); reaction time: 12 h; environment: anaerobic. The results are summarized in FIG. 16, showing that increasing the concentration of the catalyst lead to a higher yield. However, with higher loading of Cu-catalyst, more $Cu^{2+}$ were detected to remain on the film after the reaction. We found that the optimum Cu concentration was 2.5 mM. Although this concentration did not provide the highest yield, $Cu^{2+}$ were not detected on the surface, which is needed for bioapplications since copper is cytotoxide and catalyzes the degradation of the organic films.

Using the best concentration of Cu complex and running the reaction under controlled atmosphere. The effect of the reaction time on the yield was investigated (Table 2). Two sets of experiments were performed at varying reaction time (3, 6, 12 and 18 h), in the presence of Cu catalyst and ascorbic acid. Satisfactory yields (>65%) were obtained only after 12 h. The reaction stopped after ~70% conversion.

The effect of using a chelating agent to sequester $Cu^{2+}$ in the surface on the yield of the coupling reaction was considered. EDTA is a well known chelating agent of heavy metals such as $Cu^{2+}$.

Figure 17:
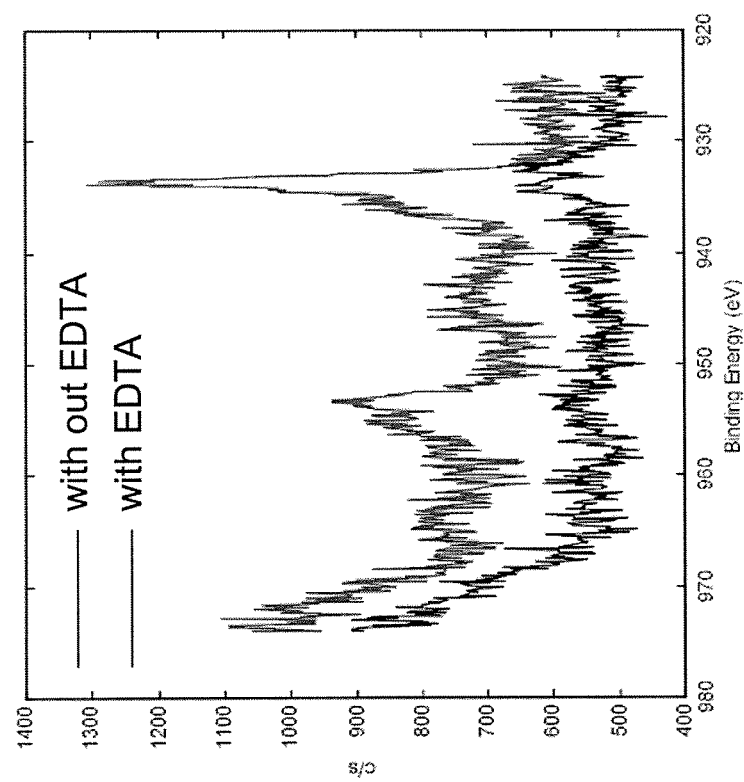
FIG. 17 shows high resolution spectra of Cu 2p of clicked surfaces on Si (111) with and without EDTA.

Two sets of measurements were performed to test the effect of adding a chelating agent in the reaction mixture (Table 3). In the first measurement, EDTA was added into the reaction mixture after 6 h of coupling. After the addition, the films were kept into the reaction vessel for another 6 h. It was mentioned from previous results that the reaction has began after 6 h though the reaction has not reached its completion. The results for the first case with EDTA showed a yield of ~46%, which is similar to the yield that was obtained for a 6 h reaction without EDTA. On the other hand, no reaction was observed after 12 h if EDTA was added at the beginning. Significantly, the addition of EDTA after the reaction greatly decreased the amount of Cu left in the film, as shown in the narrow Cu 2p scan before and after EDTA addition (FIG. 17).

Using the ligands for the Surface CuAAC Reaction.

Figure 18:
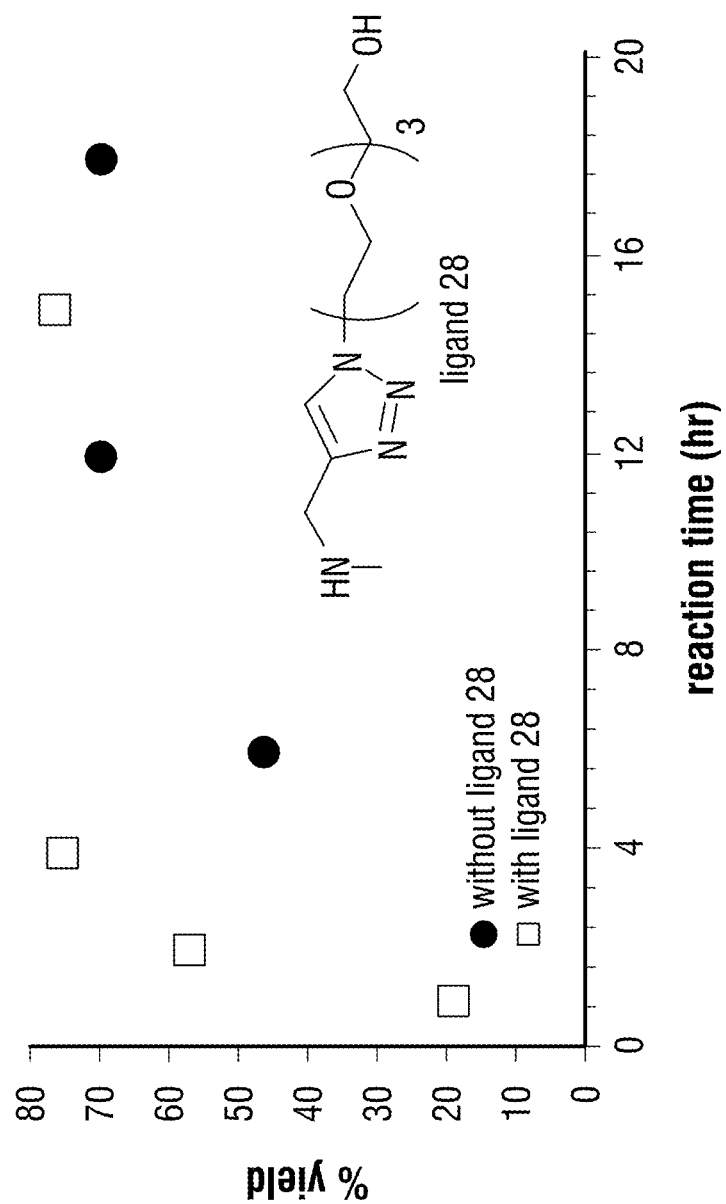
FIG. 18 shows comparison of the percent conversion of the clicked materials on Si (111) surface with and without the addition of a ligand (Top)

Referring to FIG. 18, the structure of the ligand that was used for click reaction is composed of triazole ring, an amine functionality and EG units. Conditions for the ligand based click: 200 .mu.L $Cu(MeCN)_4 PF_6$ (2.5 mM) and ascorbic acid (50 mM) in methanol; 250 .mu.L azide (10 mM) in ethanol/water (1:1 v/v); 200 .mu.L ligand 28 (25 mM); reaction time: 1, 2, 4, 15 h. Two sets of experiments were performed at reaction times of 1, 2, 4 and 15 h in the presence of the ligand 8 (FIG. 18). Evidently, the ligand accelerated the rate of the $Cu^+$ dependent process for coupling reactions interrupted after 1 h. The extent of conversion after 1 and 2 h interruptions was found to be .about.19 and .about.57%, respectively. The results showed a significant improvement in the yield as compared to the no reaction observed for a typical "ligand free" system interrupted after 3 h. Upon a 4 h cycloaddition reaction, .about.75% of the alkyne terminated monolayer was converted to the corresponding triazole product.

When prolonged reaction time was employed (15 h) no significant benefits associated with the presence of the ligand was evident.

Figure 19:
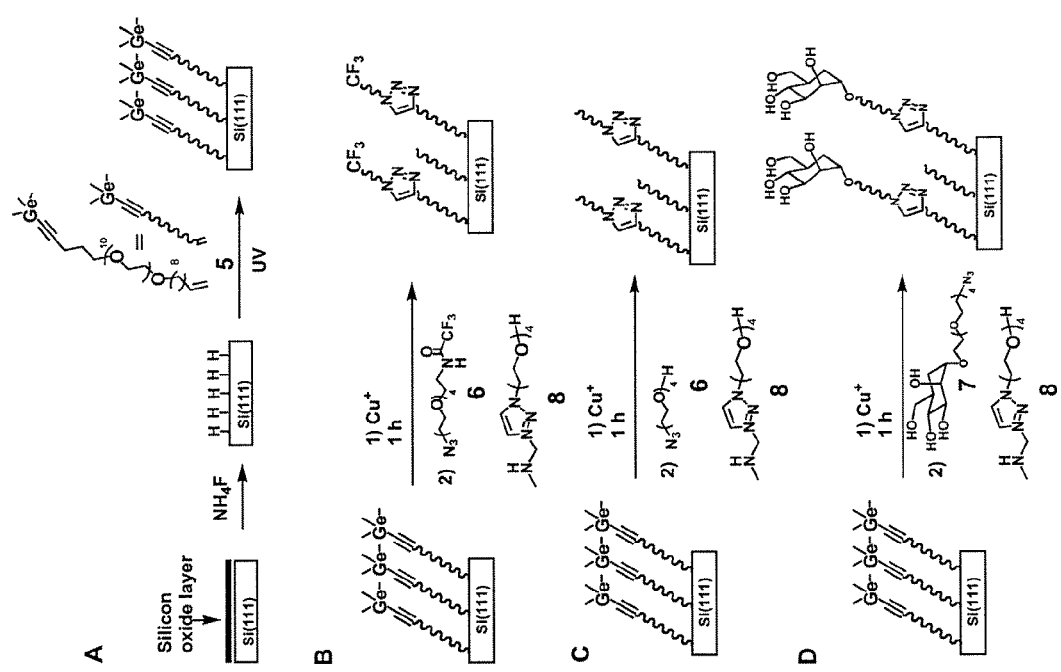
FIG. 19 shows an optimized scheme.
Figures 20A, 20B:
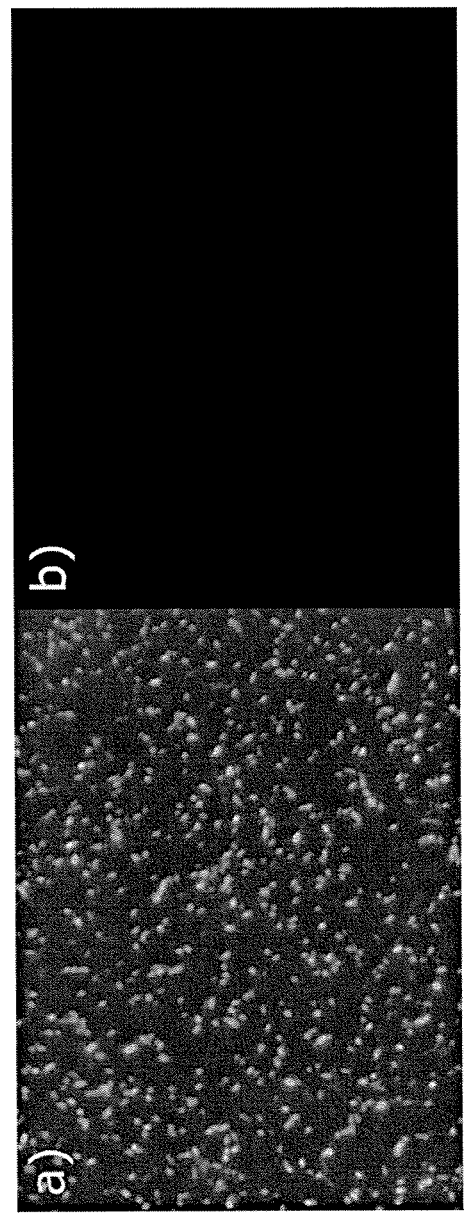
FIGS. 20$a$-$b$ show fluorescence images after incubation of films presenting mannose in *E. coli* Hu2545 (a) and Hu2634 (b)

To this end, the 4 h reaction with the ligand showed the best result for the cycloaddition reaction of EG containing alkyne and azide functionalized reacting species. A plot comparing the percent conversion of the click reaction as function of reaction time in the presence and absence of ligand depicts the remarkable improvement of the coupling yield (from 69 to 75%). More importantly, the incorporation of the ligand, greatly advanced the potential of click reaction in the surface by reducing the time of reaction by 33%. Furthermore, the amount of catalyst Demonstration of the Selective Detection of *E. coli* Using the Scheme for Biofunctionalization of Silicon Surfaces Reaction conditions were optimized (FIG. 19) for tethering the azido-OEG mannoside 7 and the azido-OEG glucose 9 onto the above monolayers presenting C≡C-TMG groups. To demonstrate the specific detection of bacteria using the functionalized surfaces, several modifications of the *Escherichia coli* strain 83972 [Andersson, P.;. Engberg, I.; Lidinjanson, G.; Lincoln, K.; Hull, R.; Hull, S.; Svanborg, C. *Infect. Immun.* 1991, 59, 2915.] were created for the study by Dr. Barbara W. Trautner at Baylor College of Medicine. In particular, *E. coli* Hu2545 overexpressing mannose-binding type 1 fimbriae [Pratt, L. A.; kolter, R. *Mol. Microbiol.* 1998, 30, 285.] by transforming *E. coli* 83972 with pSH1 (an 18 copy plasmid with the intact fim operon) were created. [Hull, R. A.; Gill, R. E.; Hsu, P.; Minshew, B. H.; Falkow, S. *Infect. Immun.* 1981, 33, 933.] *E. coli* Hu2634 is an 83972 mutant lacking fim, created by transforming *E. coli* 2222 (83972 ΔfimHΔ-papG) with pACYC184ΔTc. [Chang, A. C. Y.; Cohen, S, N. *J. Bacteriol.* 1978, 134, 1141.] Both strains were transformed with pGreen so that they fluoresced green. The mannose- and glucose presenting films and a film of 5 as control were incubated for 7 hours in Luria Bertani media containing either Hu2545 or Hu2634. As expected, the fim+ *E. coli* strain Hu2545 attached to the mannose-presenting surfaces, while the fim- strain Hu2634 did not adhere to the surfaces (FIG. 20). Both strains did not attached to the glucose-presenting surfaces. The contrast is extremely high. Furthermore, no *E. coli* Hu2545 were found on the film derived from 5; the fluorescence images (not shown) were similar to FIG. 20*b*. Referring to FIG. 20, the films were prepared by hydrosilylation of 5 on H—Si(111) and then click reaction with 7.

Applicant has shown that TMG-protected α,ω-alken-ynes undergo selective surface hydrosilylation on H-terminated silicon. Click reactions can be directly performed on the resulting monolayers presenting C≡C-TMG groups. Biomolecules can be tethered onto OEG monolayers on silicon using this method, as demonstrated by the specific adherence of *E. coli* expressing mannose-binding fimbriae onto the mannose-presenting surfaces.

Development of High Efficient Copper Catalysts for Bioconjugation onto Surfaces

Despite its popularity, there are a few drawbacks of click reactions (more accurate term is Cu-catalyzed azide-alkyne 1,3-dipolar cycloaddition (CuAAC)) for bioconjugation. First, Cu(I) catalyst is thermodynamically unstable and can be easily oxidized by oxygen in air and/or disproportionate in aqueous solution to catalytically inactive Cu(II). Reducing agents, especially ascorbic acid, are commonly used to reduce Cu(II) back to Cu(I). However, Cu(I)/ascorbate mediated degradation of the biological scaffolds has been observed. Second, Cu(I) is highly cytotoxic, thus greatly limiting the CuAAC reaction for bioconjugation in the presence of live cells. Third, the CuAAC reaction is still not a true click reaction: it is quite slow, and the yields are sometimes quite low. The objective of this project is to develop copper catalysts and conditions to allow the CuAAC reactions to complete rapidly (within a few minutes) in almost quantitative yield using a low concentration (<10 μM) of Cu(I) catalyst under philological conditions.

Recently, the Shalpless group has reported the tris(triazo) ligand 1 that significantly accelerates the CuAAC reaction and stabilizes the +1 oxidation state of the copper catalyst. Its tetradentate binding ability is believed to protect the Cu(I) center against destabilizing interactions. The tertiary amine and the [1,2,3]-triazole functionalities likely work in concert to promote the catalytic efficiency of Cu(I): the sterically encumbered N-atom of the tertiary amine accelerates the reaction by increasing the electron density on the metal center, while the weaker triazole ligand comes off the copper center temporarily to allow the formation of the Cu(I)-acetylide complex, which is then carried through the catalytic cycle. This ligand is now commercially available, and has been widely used in CuAAC reactions performed in organic solvents, although using it for bioconjugation involving nucleic acids, proteins and cells is limited.

Figure 21:
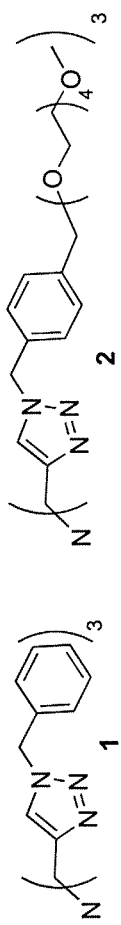
FIG. 21 shows a tris(triazole) 1 and an OEG-modified ligand 2.

Despite of its wide use, the tris(triazole) 1 (FIG. 21) is hardly soluble in water, thus limiting its utility in bioconjugation reactions. We reasoned that tethering the amphiphilic oligo(ethylene glycol) (OEG) groups to 1 would not only render its Cu(I) complex water-soluble, but also improve its biocompatibility. The synthesis of the OEG-modified ligand 2 (FIG. 21) was straightforward. Thus, monosubstitution of 1,4-bis(chloromethyl)benzene (3) with methyl tetra(ethylene glycol) 4 provided the OEG-benzyl chloride 5 in 77% yield. The azido group was readily introduced to 5 in 90% yield. 1,3-Dipolar cycloaddition of the resultant azide 6 with tripropargyl amine (7) in the presence of Cu(I) afforded the water soluble tris(triazole) ligand 2 in good yield.

Figure 22:
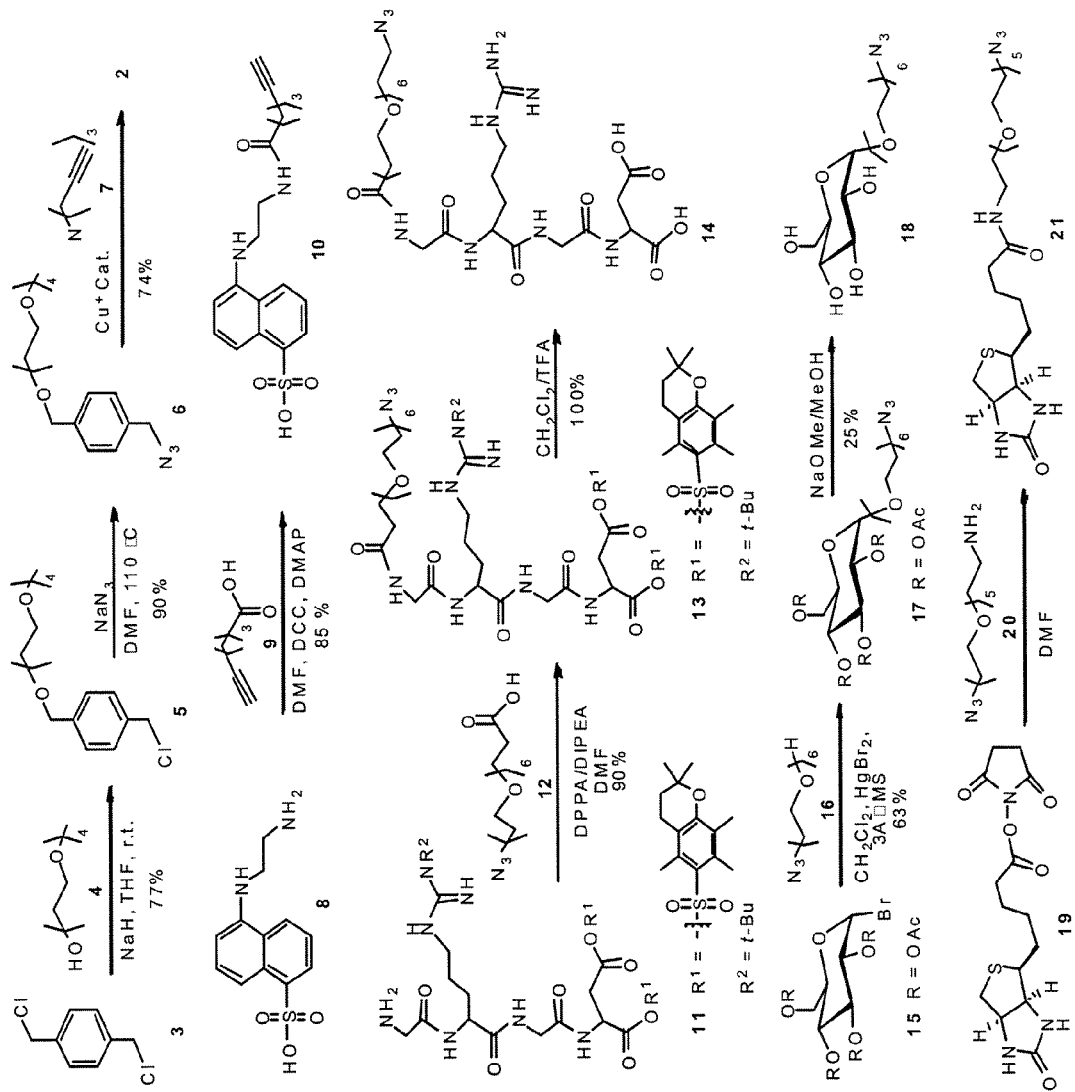
FIG. 22 shows a scheme for synthesis of the water soluble Cu(I) ligand 2 the Alkyne 10 and the Azides 14, 18, and 21.

To test the efficiency of the ligand 2, several azido derivatized biomolecules were synthesized (FIG. 22). Protected tetrapeptide GRGD 11 was attached azido modified oligoethylene glycol 12 via carbodiimide coupling to give 13 which on deprotection gave 14.

Similarly acetate protected bromide derivative of glucose 15 was attached to azido modified oligoethylene glycol 16 to give 17 which on deprotection gave azido modified glucose 18. On the same line biotin-NHS 19 was attached with azido modified oligoethylene glycol 20 to give azido modified biotin. Florescent dye 8 was coupled with hexynoic acid (9) via carbodiimide chemistry to give alkyne terminated dye 10.

The CuAAC reactions of these azides with in the presence of the ligand 2 in aqueous medium under ambient conditions to give products 22, 23 and 24 in excellent yields (FIG. 22).

Figure 23:
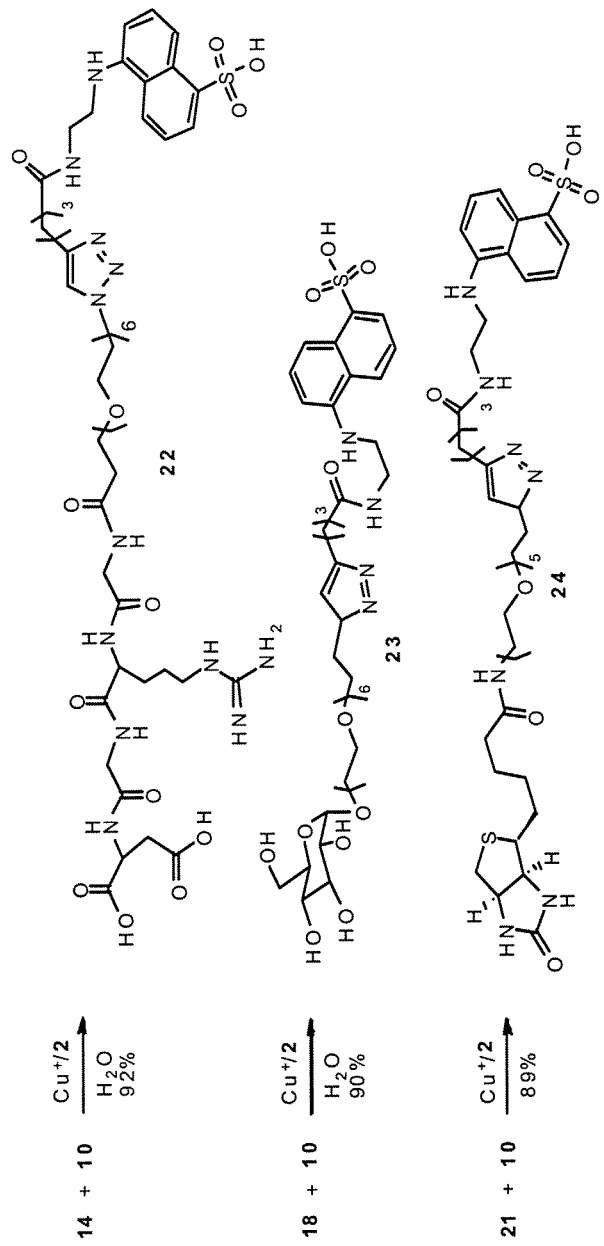
FIG. 23 shows a scheme for CuCCA reactions of the Alkyne 10 with the Azides 14, 18, and 21.

Although the tris(triazo) ligands 1 and 2 greatly accelerate the rate of CuAAC under ambient conditions with excellent yields, the reaction is still relatively slow (>12 hours for completion, FIG. 23). In addition, we observed that 2 did not promote the CuAAC reaction on monolayers presenting ethynyl groups, probably due to the steric hindrance. Finn and other groups have reported more efficient ligands for CuAAC reaction, especially the water soluble bathophenanthroline and Benzimidazole. The rate enhancement of these ligands is apparently attributed to the electron-donating amino groups. Aliphatic amines and pyridine derivatives have been used as ligands of Cu(I) and/or protic bases to enhance the CuAAC reaction, but the results are often not satisfactory. Unfortunately, the stronger electron-donating ability of the ligands also render their Cu(I) complexes extremely sensitive to oxygen. To solve this problem, we used Oxyrase to remove oxygen in the solution. Oxyrase is prepared from *Enterococcus* coli, and contains enzymes that catalyze the reduction of $O_2$ in water in the presence of a hydride source such as lactic acid.

Figure 25:
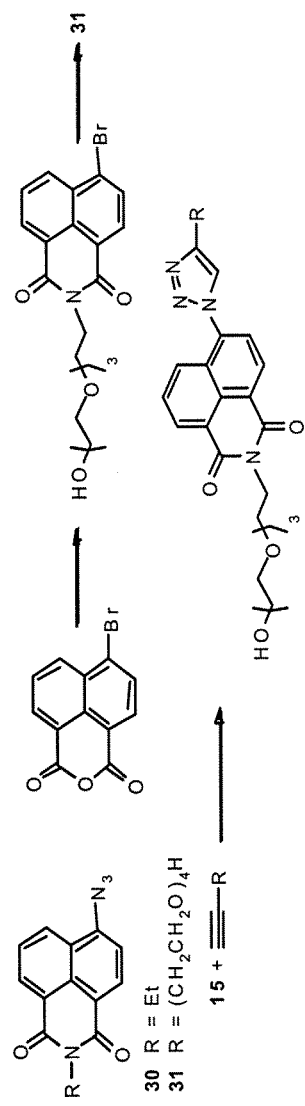
FIG. 25 shows a scheme for synthesis of the Azide 15 for Screen the Ligands of CuAAC reactions.

To screen these ligands, click-activated fluorogenic labeling technique was used. This method was reported by wong et. al. involves the use of 1,8-naphthalimide derivative 30 (FIG. 25) designed for click-activated fluorescence with an azide moiety attached at the 4 position.

Figure 24:
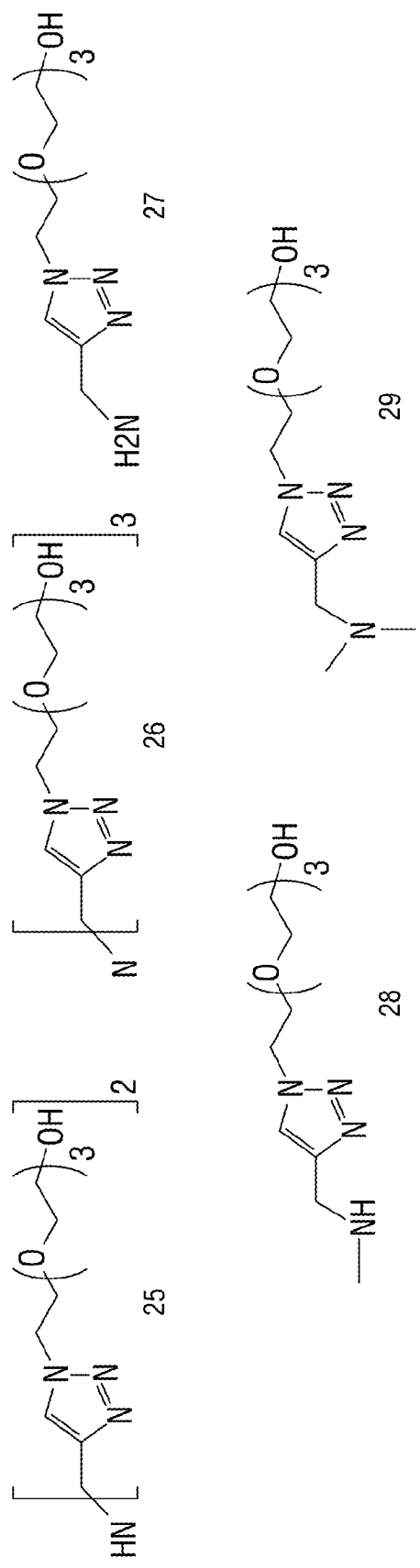
FIG. 24 shows ligands Screened for CuAAC.

We modified the reported probe to be water soluble 31 (FIG. 25) so that rate of click chemistry could be followed in aqueous media. The water soluble azido modified 1,8-naphthalimide derivative has a absorption maxima at 355 nm and emission at 422 nm. The increase of florescence over time indicates the rate of reaction. Under ambient conditions OEG derivative of TBTA 2 performed the best but under anaerobic condition ligand 28 (FIG. 24) was found to perform better.

In our system, the ligand that we have used has a triazole ring, an amine functionality and an EG units. The ring stabilizes the $Cu^+$ by forming a complex, which encapsulates Cu thereby preventing it from oxidizing. The additional N, which is not from the ring donates e-s to Cu thus making it more labile and increases the rate of reaction. The EG functionality was incorporated to increase its solubility in water making it biocompatible.

Experimental Section

General information: Air sensitive reactions were performed under a nitrogen atmosphere using Schlenk technique. All reagents were purchased from Sigma-Aldrich or Alfa Aesar, and used without purification. Flash chromatography was carried out on silica gel (60 Å, Sorbent Technologies). All $^1$H- and $^{13}$C-NMR spectra were recorded in $CDCl_3$ using residual $CHCl_3$ as internal standard. Mass spectroscopy (MS) measurement was carried out using electrospray ionization (ESI) technique. Usual workup procedure: The reaction was quenched with water, and the mixture was extracted with $3\times CH_2Cl_2$. The organic layers were combined, washed with water and brine, dried over $Na_2SO_4$ or $Mg_2SO_4$, and filtered.

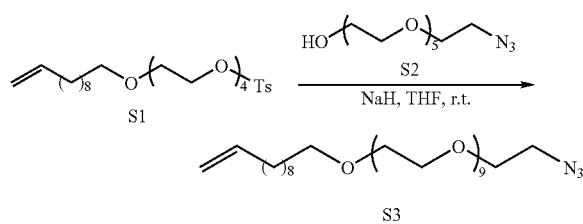

A soln. of S2[1] (317 mg, 1.0 mmol) in dry THF (3 mL) was added to NaH (18 mg, 0.75 mmol) under $N_2$. After stirring for 4 h, the mixture was treated with a soln. of S1[2] (375 mg, 0.75 mmol) in dry THF (2 mL), and stirred for 48 h at room temperature. Usually workup and flash chromatography (ethyl acetate/methanol=30/1) provided S3 as a colorless oil (184 mg, 58% yield). $^1$H NMR (300 MHz, $CDCl_3$) δ 1.16-1.31 (m, 12H), 1.47-1.54 (m, 2H), 1.95-2.02 (m, 2H), 3.32-3.41 (m, 4H), 3.50-3.83 (m, 38H), 4.86-4.97 (m, 2H), 5.69-5.80 (m, 1H). $^{13}$C NMR (75 MHz, $CDCl_3$) δ 25.9, 28.8, 28.9, 29.26, 29.29, 29.4, 29.5, 33.6, 50.5, 69.87, 69.90, 70.42, 70.47, 70.52, 70.54, 71.4, 113.9, 139.0. ESI-MS: m/z 658 $[M+Na]^+$.

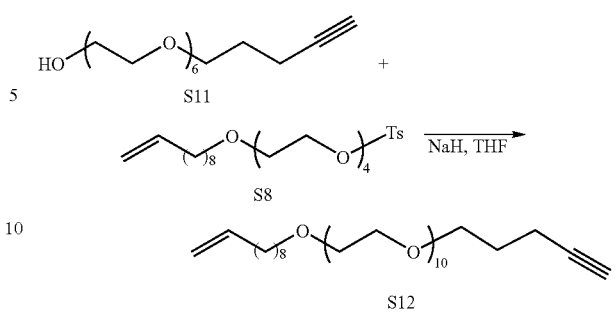

To a soln. of S11 (0.8 g, 2.3 mmol) in dry THF (10 mL) was added NaH (200 mg, 5.0 mmol, 57-63% in oil) under nitrogen at 0° C. The mixture was stirred for 1 h, treated with a soln. of S8 (1.1 g, 2.3 mmol) in dry THF (10 mL), and stirred at room temperature overnight. The reaction was quenched by water. The mixture was extracted with $CH_2Cl_2$ (3×30 mL). The organic layers were combined, washed with water (30 mL) and brine (30 mL), dried over $Na_2SO_4$, and filtered. The residue was purified by flash chromatography (ethyl acetate/methanol=20/1) to give S12 (1.1 g, 72% yield) as light yellow oil. $^1$H NMR (300 MHz, $CDCl_3$) δ 1.28-1.38 (m, 10H), 1.54-1.62 (m, 2H), 1.79 (tt, J=6.0, 6.6 Hz, 2H), 1.94 (t, J=2.7 Hz, 1H), 2.03 (q, J=6.6 Hz, 2H), 2.28 (dt, J=2.7, 6.9 Hz, 2H), 3.44 (t, J=6.9 Hz, 2H), 3.53-3.70 (m, 42H), 4.90-5.02 (m, 2H), 5.74-5.87 (m, 1H). $^{13}$C NMR (75 MHz, $CDCl_3$) δ 15.0, 25.9, 28.3, 28.7, 28.9, 29.2, 29.4, 33.6, 68.3, 69.3, 69.9, 70.0, 70.35, 70.40, 71.3, 83.7, 113.9, 139.0. ESI-MS: m/z 685 $[M+Na]^+$.

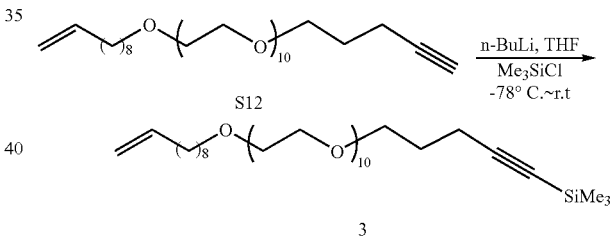

At −78° C., n-butyllithium (2.2 M in hexane, 1.1 mL, 2.4 mmol) was added to a solution of S12 (200 mg, 0.3 mmol) in dry THF (20 mL) in the presence of 3 Å MS (20 mg). After stirring for 1 h at this temperature, chlorotrimethylsilane (261 mg, 2.4 mmol) was added. The reaction mixture was warmed to room temperature and stirred overnight. The reaction mixture was purified by flash chromatography (ethyl acetate/methanol=100/3) to afford 3 (150 mg, 68% yield) as light yellow oil. $^1$H NMR (300 MHz, $CDCl_3$) δ 0.14 (s, 9H), 1.25-1.41 (m, 10H), 1.51-1.62 (m, 2H), 1.75-1.82 (m, 2H), 2.00-2.08 (m, 2H), 2.31 (t, J=6.6 Hz, 2H), 3.44 (t, J=6.6 Hz, 2H), 3.52-3.71 (m, 42H), 4.90-5.01 (m, 2H), 5.74-5.87 (m, 1H). $^{13}$C NMR (75 MHz, $CDCl_3$) δ 0.0, 16.4, 25.8, 28.4, 28.7, 28.8, 29.2, 29.4, 33.6, 69.4, 69.8, 70.0, 70.4, 71.3, 84.4, 106.6, 113.9, 138.9. ESI-MS: m/z 758 $[M+Na]^+$.

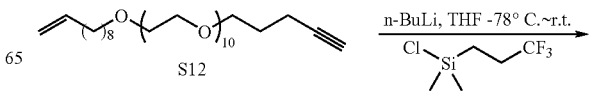

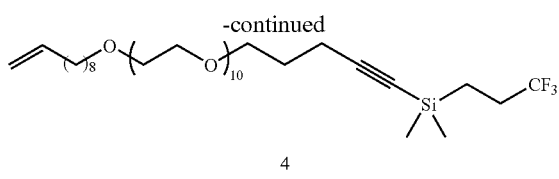

4

At −78° C., n-butyllithium (2.2 M in hexane, 1.1 mL, 2.4 mmol) was added to a solution of S12 (200 mg, 0.3 mmol) in dry THF (20 mL) with 3 Å MS (20 mg). After stirring for 1 h at this temperature, chlorodimethyl-3,3,3-trifluoropropylsilane (419 mg, 2.2 mmol) was added. The reaction mixture was warmed to room temperature and stirred over night. Usual workup and flash chromatography (ethyl acetate/methanol=100/3) afforded 4 (50 mg, 20% yield) as colorless oil. $^1$H NMR (300 MHz, CDCl$_3$) δ 0.15 (s, 6H), 0.75-0.81 (m, 2H), 1.23-1.37 (m, 10H), 1.51-1.58 (m, 2H), 1.73-1.82 (m, 2H), 1.98-2.14 (m, 4H), 2.31 (t, J=7.2 Hz, 2H), 3.43 (t, J=6.6 Hz, 2H), 3.50-3.69 (m, 42H), 4.89-5.00 (m, 2H), 5.72-5.86 (m, 1H). ESI-MS: m/z 841 [M+Na]$^+$.

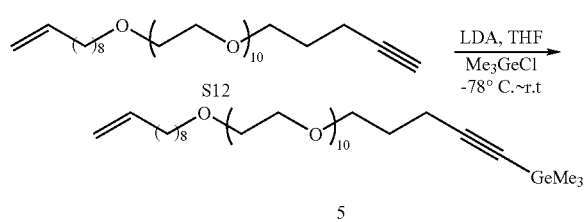

5

At −76° C., to a stirred soln. of S12 (51 mg, 0.077 mmol) in dry THF (1 ml) under nitrogen was added a soln. of LDA (1.8 M in THF/benzene/haptane, 0.12 ml, 0.216 mmol). After stirring for 2 h at −76° C., Me$_3$GeCl (32 μl, 0.259 mmol) was added. The mixture was stirred at −76° C. for 2 h, and allowed to warm up to room temperature and stirred overnight. Usual workup and flash chromatography (methanol/ethyl acetate=1/99) afforded 5 (22 mg, 37% yield) as pale yellow oil. $^1$H-NMR (300 MHz, CDCl$_3$) δ 0.30 (s, 9H), 1.24-1.37 (m, 12H), 1.53-1.58 (m, 2H), 1.72-1.80 (m, 2H), 1.98-2.05 (m, 2H), 2.29 (t, J=6.9 Hz, 2H), 3.43 (t, J=6.6 Hz, 2H), 3.50-3.64 (m, 40H), 4.89-5.01 (m, 2H), 5.72-5.86 (m, 1H).) $^{13}$C-NMR (300 MHz, CDCl$_3$) δ 26.06, 28.76, 28.89, 29.04, 29.42, 29.61, 33.78, 69.79, 70.02, 7.17, 70.54-70.59 (m), 71.51, 84.29, 105.24, 114.10, 139.18. MS (ESI): m/z 798 [M+H$_2$O]$^+$.

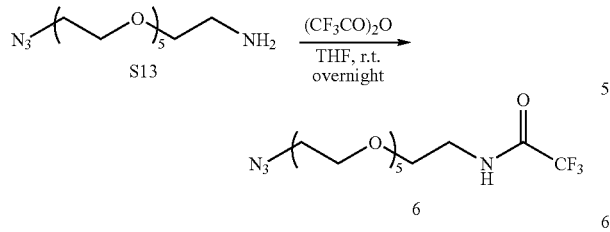

6

To a solution of S13$^4$ (100 mg, 0.37 mmol) in dry THF (1.0 mL) at room temperature was added trifluoroacetic anhydride (116 mg, 0.56 mmol). The reaction mixture was stirred overnight, concentrated in vacuum. The residue was purified by silica gel column chromatography to give 6 (141 mg, 95%) as a colorless liquid. $^1$H NMR (300 MHz, CDCl$_3$) δ 7.26-7.40 (m, 1H), 3.69-3.56 (m, 20H), 3.53-3.50 (m, 2H), 3.34 (m, 2H); $^{13}$C NMR (75 MHz, CDCl3) δ 157.3 (q, J=37.5 Hz), 115.9 (d, J=287 Hz), 71.2, 70.6, 70.5, 70.5, 70.4, 70.3, 70.2, 69.9, 68.8, 50.6, 39.7. ESI-MS: m/z 425 [M+Na]$^+$.

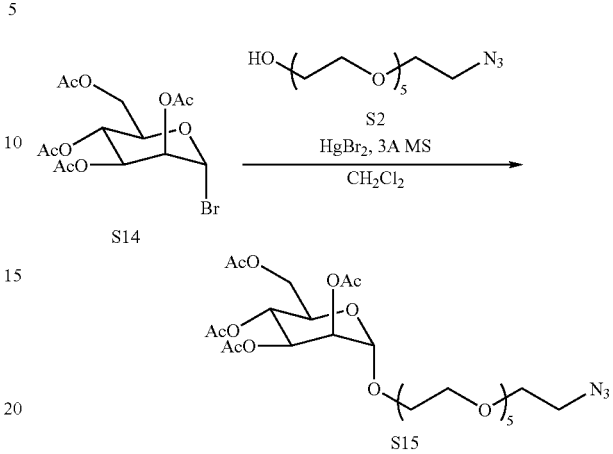

Powdered molecular sieves (3 Å) and S2 (308 mg, 0.875 mmol) were added to a stirred solution of S14 (240 mg, 0.584 mmol) in dry CH$_2$Cl$_2$ (5 mL). After 15 min, HgBr$_2$ (210 mg, 0.584 mmol) was added. The mixture was stirred overnight, diluted with CH$_2$Cl$_2$ (20 mL) and filtered over a pad of celite. The organic phase was washed with 5% KI (3×15 mL) and water (3×15 mL), dried over Na$_2$SO$_4$. Flash chromatography (EtOAc: CH$_2$Cl$_2$=1:1) provided S15 (150 mg, 40%) as light yellow oil. $^1$H NMR (300 MHz, CDCl$_3$) δ 2.00 (s, 3H), 2.05 (s, 3H), 2.11 (s, 3H), 2.16 (s, 3H), 3.46 (t, J=4.8 Hz, 2H), 3.68-3.73 (m, 26H), 4.06-4.12 (m, 2H), 4.30 (dd, J=6.0, 12.9 Hz, 1H), 4.88 (s, 1H), 5.26-5.33 (m, 3H). $^{13}$C NMR (75 MHz, CDCl$_3$) δ 20.58, 20.63, 20.7, 20.8, 50.6, 62.5, 63.4, 66.2, 67.0, 68.6, 69.1, 69.2, 69.5, 69.66, 69.71, 69.73, 69.8, 69.9, 70.0, 97.5, 169.6, 169.9, 170.0, 170.6. ESI-MS: m/z 638 [M+1]$^+$. ESI-HRMS: Calcd. for C$_{26}$H$_{44}$O$_{15}$N$_3$: 638.2774; found: m/z 638.2645.

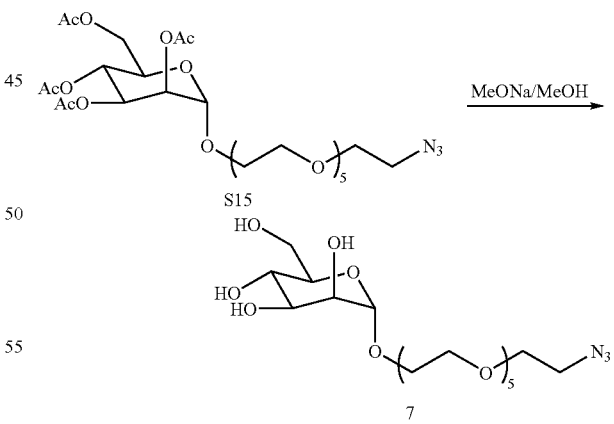

To a solution of S15 (110 mg, 0.18 mmol) in MeOH (4 mL) was added MeONa (49 mg, 0.72 mmol) at 0° C. The mixture was allowed to warm to room temperature and stirred overnight. The mixture was diluted with ether, and neutralized with HCl. Flash chromatography (EtOAc:MeOH=20:1 to 15:1) provided 7 (40 mg, 48% yield) as colorless oil. $^1$H NMR (300 MHz, CDCl$_3$) δ 3.41 (t, J=5.4 Hz, 2H), 3.58-3.71 (m, 24H), 3.89 (s, 2H), 4.00 (s, 2H), 4.89 (s, 1H), 6.27 (s, 5H). $^{13}$C NMR (75 MHz, CDCl₃) δ 50.6, 60.0, 65.9, 66.7, 69.8, 70.1, 70.2, 70.35, 70.44, 72.4, 100.0. ESI-MS: m/z 492 [M+Na]$^+$.

General Procedure for Surface Hydrosilylation to Deposit TMG-terminated Monolayer on Hydrogen-Terminated Silicon (111) Surfaces Briefly, a commercial silicon (111) wafer (single side polished Si, thickness of 500-550 μm, boron-doped (p-type), 1-10 Ω-cm resistivity, miscut angle±0.5°) was cut into pieces of 2×2 cm², and cleaned with Piranha solution (concentrated H₂SO₄ and 30% H₂O₂ 3:1 (v/v)) at 80° C. for 20-30 minutes to remove organic contaminates. (Caution: since Piranha solution reacts violently with many organic compounds, extreme care must be taken when handling it). The freshly cleaned sample was immersed in an Argon-saturated, 40% NH₄F solution for 15 min followed by rapid rinse with Argon-saturated Millipore water and dried with a stream of nitrogen. This H—Si substrate was immediately transferred into our home-built vacuum chamber. After degassed for 10 min at 10⁻⁴ Torr, the substrate was brought in contact with a droplet (ca. 2-3 mg) of alkenes 2, 3, 4, or 5 on a quartz window, forming a uniform layer of the alkene sandwiched by the quartz window and the silicon substrate. Hydrosilylation was performed under 254 nm UV illumination for 2 h. The sample was washed thoroughly with dichloromethane and absolute alcohol followed by drying under a stream of argon.

Surface Click reaction. In a typical procedure, to a 4 ml vial containing the TMG-terminated Si (111) substrate as prepared above were added 200 .mu.L of Cu(MeCN).sub.4 PF.sub.6 (5 mM), the Cu(I) ligand 28 (25 mM), and ascorbic acid (50 mM) in degassed methanol. Note: The methanol was freeze-thaw pumped for at least 6.times. prior to mixing. After incubation for 10 minutes, 250 .mu.L of the CF.sub.3-terminated azide 6 (10 mM) in ethanol/water (1:1 v/v) was added. After incubation for 4 h under inert (N.sub.2) atmosphere, 200 .mu.L of 5 mM N,N,N',N'-tetramethylethane-1,2-diamine (EDTA) was added. The sample was taken out and washed by sonication for 10 seconds in a mixture of ethanol and methanol (about.1:1 v/v) and then Millipore water. Finally, the films were dried under a stream of argon.

X-ray photoelectron spectroscopy (XPS). A PHI 5700 X-ray photoelectron spectrometer, equipped with a monochromatic AlKα X-ray source (hv=1486.7 eV) at a take-off angle (TOA) of 45° from the film surface, was employed for XPS measurement. High-resolution XPS spectra were obtained by applying a window pass energy of 23.5 eV and the following numbers of scans: Si2p, 3 scans; C1s, 6 scans; O1s, 3 scans; N1s, 30 scans; Ge3d, 15 scans; F1s, 6 scans. The binding energy scales were referenced to the Si2p peak at 99.0 eV. XPS spectra were curve fitted and the intensities measured as peak areas were calculated using Phi Multipak V5.0A from Physical Electronics.

Ellipsometry. An ellipsometer (Rudolph Research, Auto EL III), operated with a 632.8 nm He—Ne laser at an incident angle of 70°, was employed for thickness measurement. The refractive index of the silicon films was 3.839. At least there measurements were taken for each sample, and the mean values were reproducible within ±1 Å.

Atomic Force Microscopy. The films obtained before and after click reaction were examined using a MultiMode (Digital Instruments Inc., Santa Barbara, Calif., USA) atomic force microscope with a Nanoscope IIIa (Digital Instruments Inc) controller and a scanner with a maximum xy scan range of 17×17 μm. Images were acquired in tapping mode using a silicon nitride cantilever (MikroMasch, San Jose, Calif., USA) with a resonance frequency of 132.9 KHz and a nominal force constant of 1.75 N/m. Depending on the image scanned, the scan area varied from 250 nm²-10 μm² and the scanning rate from 1.97-1.49 Hz. Initially, the samples were scanned in a large area (10 μm×10 μm) at several locations to verify the homogeneity of the surface. Then, high resolution scans were performed at slower scan rate (1.49 Hz) to obtain representative images of the acquired films.

Fluorescence microscopy. Fluorescence images were obtained with an Olympus BX 51 fluorescence microscope with a 60× objective. Filter FITC was used for exciting GFP. The exposure time for the acquisition of each image was 0.01-1 s. Images were processed using QCapture software.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A sensor comprising:
   a) a silicon (Si) substrate having a surface; and
   b) a monolayer of oligoethylene glycol (OEG) bonded to the surface via silicon-carbon bonds;
      wherein regions of the OEG monolayer distal to the surface are functionalized with a molecular probe serving as a recognition element for a bioanalyte; and
      wherein said molecular probe is covalently bonded to said regions as a cycloadduct of a 1,3-dipolar cycloaddition reaction; and
      wherein the sensor is made by a method comprising allowing said 1,3-dipolar cycloaddition reaction to occur in the presence of a catalyst comprising Cu(I) and a ligand, wherein the ligand is selected from among

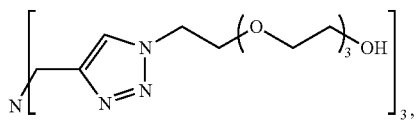

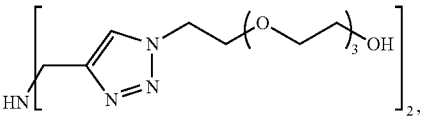

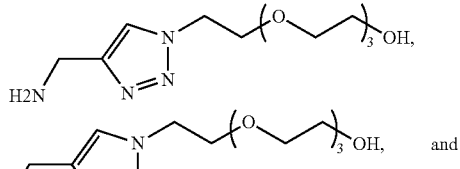

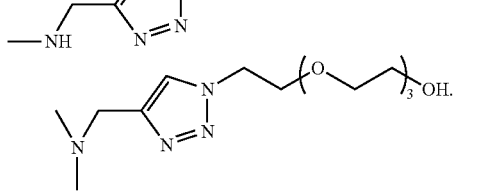

2. The sensor of claim 1, wherein the surface is atomically flat.

3. The sensor of claim 1, wherein the surface is selected from the group consisting of (100), (111), and combinations thereof.

4. The sensor of claim 1, wherein the molecular probe comprises a biomolecule selected from the group consisting of carbohydrates, proteins, oligonucleotides, and combinations thereof.

5. The sensor of claim 4, wherein the biomolecule is mannose.

6. The sensor of claim 5, wherein the bioanalyte is *E. Coli*.

7. The sensor of claim 1, wherein said 1,3-dipolar cycloaddition reaction occurs under conditions preventing detection of $Cu^{2+}$ on the surface.

8. The sensor of claim 1, wherein said OEG monolayer is stable under biological conditions.

9. The sensor of claim 8, wherein said OEG monolayer is 97% resistance to protein adsorption in cell culture for 17 days.

10. The sensor according to claim 1, wherein said surface is unoxidized.

11. A silicon surface modified to interact with a biological specimen made by the process comprising:
    hydrosilylating with a mixture comprising:
        an oligoethylene glycol (OEG) substituted with an alkene at one end of the OEG and capped at the opposing end of the OEG; and
        an oligoethylene glycol (OEG) substituted with an alkene at one end of the OEG and an alkyne having a protecting group at the opposing end of the OEG;
    removing the protecting group from the alkyne without oxidizing the silicon surface; and
    reacting the alkyne with a reagent in a 1,3-dipolar cycloaddition;
    wherein the reagent in the 1,3-dipolar cycloaddition comprises a portion capable of being recognized by a biological specimen, wherein the removing and reacting occur in one step in the presence of a catalyst comprising Cu(I) and a ligand, wherein the ligand is selected from among

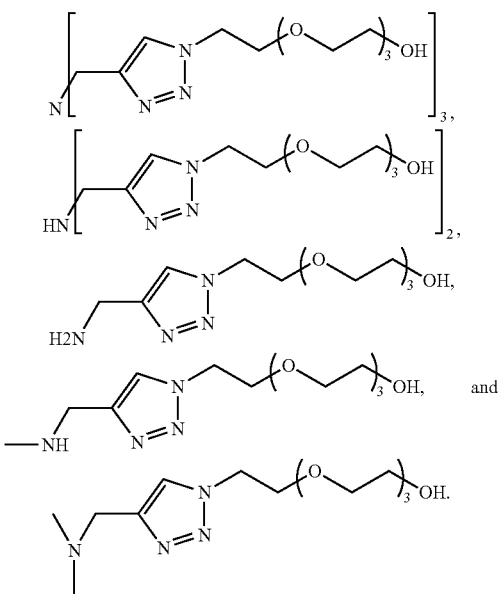

12. The silicon surface according to claim 11, wherein the removing and reacting occur under conditions preventing detection of $Cu^{2+}$ on the surface.

13. The silicon surface according to claim 12, wherein the removing and reacting occur under physiological conditions.

14. The silicon surface of claim 11, wherein the reagent in the 1,3-dipolar cycloaddition further comprises a reactive functional group selected from the group consisting of an azide, a nitrile oxide, an azomethine ylide, a carbonyl ylide, and a nitrone.

15. The silicon surface of claim 14, wherein the reactive functional group is an azide as the reactive functional group.

16. The silicon surface of claim 11, wherein the biological specimen is selected from the group consisting of a bacterium, a virus, a protein, a DNA sequence, a RNA sequence, and an oligosaccharide.

\* \* \* \* \*